(12) United States Patent
Jain et al.

(10) Patent No.: US 7,790,895 B2
(45) Date of Patent: Sep. 7, 2010

(54) QUINOLINE DERIVATIVES AS POTASSIUM ION CHANNEL OPENERS

(75) Inventors: Nareshkumar Jain, Exton, PA (US); Jiayi Xu, Palo Alto, CA (US); Zhihua Sui, Exton, PA (US)

(73) Assignee: Janssen Pharmaceutica NV (BE)

( * ) Notice: Subject to any disclaimer, the term of this patent is extended or adjusted under 35 U.S.C. 154(b) by 1233 days.

(21) Appl. No.: 11/360,084

(22) Filed: Feb. 23, 2006

(65) Prior Publication Data

US 2007/0054936 A1    Mar. 8, 2007

Related U.S. Application Data

(60) Provisional application No. 60/655,763, filed on Feb. 24, 2005.

(51) Int. Cl.
*C07D 215/38* (2006.01)
(52) U.S. Cl. ...................................... 546/170
(58) Field of Classification Search ................ 546/170
See application file for complete search history.

(56) References Cited

U.S. PATENT DOCUMENTS 5,710,162 A * 1/1998 Okazaki et al. ............. 514/280

FOREIGN PATENT DOCUMENTS

WO    WO 98/23273  A1    6/1998

OTHER PUBLICATIONS

Tawada, CA 123:339669, Abstract only of Chem & Pharm Bull, 43(4), pp. 616-625, 1995.*
Aguilar-Bryan, L et al.: "Toward Understanding the Assembly and Structure of $K_{ATP}$ Channels"; Physiol. Rev., (1998) 78(1): 227-245.
Kelly, T.R. et al.: "Synthesis of Schumanniophytine and Isoschumannlophytine"; J. Org. Chem. 1992 57: 1593-1597.
Nadin, A. et al.: "Synthesis of Tricyclic Pyridones by Radical Cyclization"; Tetrahedron Letters (1999) 40: 4073-4076.
Wein, A.J.: "Overactive Bladder: Defining the Disease", Am. J. of Managed Care (2000) vol. 6, No. 11:S559-564.
PCT International Search Report for PCT International Appln No. PCT/US2006/006515 dated Jun. 29, 2006.

* cited by examiner

*Primary Examiner*—D. Margaret Seaman
(74) *Attorney, Agent, or Firm*—Joseph S. Kentoffio; Jeremy K. McKown

(57) ABSTRACT

The present invention is directed to novel quinoline derivatives, pharmaceutical compositions containing them and their use in the treatment of disorders related to ion channels such as potassium channels.

7 Claims, No Drawings

QUINOLINE DERIVATIVES AS POTASSIUM ION CHANNEL OPENERS

CROSS REFERENCE TO RELATED APPLICATIONS

This application claims the benefit of U.S. Provisional Application 60/655,763, filed on Feb. 24, 2005, which is incorporated by reference herein in its entirety.

FIELD OF THE INVENTION

The present invention is directed to novel pyridine and quinoline derivatives, pharmaceutical compositions containing them and their use in the treatment of disorders related to ion channels such as potassium channels. The compounds of the invention are thus useful for the treatment of various disorders, including, but is not limited to, urinary incontinence, overactive bladder, hypertension, erectile dysfunction, benign prostate hyperplasia, female sexual disorders, premature labor, dysmenorrhea, irritable bowel syndrome, airway hyperactivity, epilepsy, stroke, ischemia, Alzheimer's disease, Parkinson's diseases, myocardial injury, coronary artery disease, angina, pain, eating disorders, hair loss, alopecia and baldness.

BACKGROUND OF THE INVENTION

Ion channels play a fundamental role in the hormeostasis of cell function through the regulation of the transmembrane movement of ions. Cellular activity can be affected by modifications of the activities of the ion channels. This leads to changes in membrane potential difference. Potassium channels are a diverse and ubiquitous group of ion channels. They principally regulate the resting membrane potential of the cell and attenuate the level of excitation of cells. A functional $K_{ATP}$ channel is a hetero-octamer assembled from four inward rectifying potassium channel subunits (Kir6.2) and four sulfonylurea receptor (SUR) subunits. There are two SUR genes, SUR1 and SUR2. SUR1/Kir6.2 channels are found in the pancreas and brain. Two major splice variants arise from the SUR2 gene, SUR2A and SUR2B, that differ only at the C-terminal 42 amino acids. SUR2A/Kir6.2 channels are found in cardiac and skeletal tissues whereas SUR2B/Kir6.2 channels are found in smooth muscles of many tissues including bladder (Aguilar-Bryan, L.; Clement J. P.; Gonzales, G. et al. (1998) "Toward understanding the assembly and structure of $K_{ATP}$ channels" Physiol. Rev. 8:227-245). A number of diseases or conditions may be treated with potassium channel openers. These includes overactive bladder, urinary incontinence, male erectile dysfunction, female sexual disorders, premature labor, benign prostate hyperplasia (BPH), dysmenorrhea, neurodegeneration, stroke, pain, coronary artery disease, angina, ischemia, eating disorders, irritable bowel syndrome and alopecia.

Urinary incontinence (UI) is a disease that can affect the overall quality of life of a patient. Overactive bladder (OAB) is the most prevalent form of UI, with reported prevalence rate from 40 to 70% of all diagnosed UI cases (Wein, A. J. (2000) "Overactive bladder: defining the disease" Am. J. Manag. Care. 6:S559-564). OAB is characterized by the symptoms of increased urinary frequency, urgency, and involuntary loss of urine. A primary cause of OAB is an oversensitive bladder that contracts unexpectedly and involuntarily. The ideal pharmaceutical agent should suppress the involuntary contraction while leaving the normal voiding contractions intact. ATP-sensitive potassium channel openers (KCO) could serve as such agents. The ATP-sensitive potassium channels ($K_{ATP}$) are expressed in bladder smooth muscle and function as key regulators of the resting membrane potential in these cells. Compounds that selectively open these channels hyperpolarize the cell and decrease cellular excitability, resulting in suppression of involuntary bladder contractions, while leaving the normal micturition circuitry intact.

SUMMARY OF THE INVENTION

The present invention is directed to compounds of formula (I)

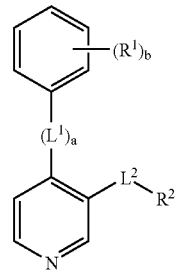

wherein a is an integer from 0 to 1;

$L^1$ is selected from the group consisting of —C(O)— and CH(OH)—;

b is an integer from 0 to 2;

$R^1$ is selected from the group consisting of halogen, alkyl, halogenated alkyl, hydroxy substituted alkyl, alkoxy, cyano, alkyl-carbonyl-, alkoxy-carbonyl-, formyl and phenyl;

$L^2$ is selected from the group consisting of —C(O)—, —CH(OH)— and —CH$_2$—;

alternatively, $L^1$ and $L^2$ are taken together to form a 5-membered oxygen containing ring;

$R^2$ is selected from the group consisting of hydrogen, hydroxy, alkyl, trifluoromethyl, aryl and t-butyl-dimethylsilyloxy;

wherein the aryl is optionally substituted with one or more substituents independently selected from halogen, alkyl, alkoxy, alkylthio-, amino, alkylamino or dialkylamino;

provided that when $R^2$ is hydroxy, then $L^1$ and $L^2$ are taken together to form a 5-membered oxygen containing ring;

provided further that when a is 1, $L^1$ is —CH(OH)—, b is 1, $R^1$ is $CF_3$ and $L^2$ is $CH_2$, then $R^2$ is other than alkyl;

provided further that when a is 1, $L^1$ is —C(O)—, b is 1, $R^1$ is alkoxy and $L^2$ is —CH(OH)—, then $R^2$ is other than hydrogen;

provided further that when a is 1, $L^1$ is —C(O)—, b is an integer from 0 to 1, $R^1$ is halogen, alkoxy, $CF_3$ or amino and $L^2$ is —CH$_2$—, then $R^2$ is other than hydrogen or alkyl;

and pharmaceutically acceptable salts thereof.

The present invention is further directed to compounds of formula (II)

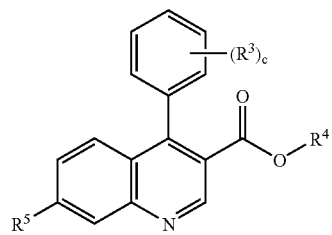

(II)

wherein c is an integer from 0 to 2;

R³ is selected from the group consisting of halogen, alkyl, halogenated alkyl, hydroxy substituted alkyl, alkoxy, cyano, alkyl-carbonyl-, alkoxy-carbonyl-, formyl and phenyl;

R⁴ is selected from the group consisting of $C_{1-4}$alkyl;

R⁵ is selected from the group consisting of methyl and trifluoromethyl;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders mediated by an ion channel, preferably a potassium ion channel, more preferably an ATP-sensitive potassium ion channel, in a subject in need thereof comprising administering to the subject a therapeutically effective amount of any of the compounds or pharmaceutical compositions described above.

An example of the invention is a method for treating a disorder selected from the group consisting of urinary incontinence, overactive bladder, hypertension, erectile dysfunction, benign prostate hyperplasia, female sexual disorders, premature labor, dysmenorrhea, irritable bowl syndrome, airway hyperactivity, epilepsy, stroke, ischemia, Alzheimer's disease, Parkinson's diseases, myocardial injury, coronary artery disease, angina, pain, eating disorders, hair loss, alopecia and baldness, preferably urinary incontinence or overactive bladder, in a subject in need thereof comprising administering to the subject an effective amount of any of the compounds or pharmaceutical compositions described above.

Another example of the invention is the use of any of the compounds described herein in the preparation of a medicament for treating: (a) urinary incontinence, (b) overactive bladder, (c) hypertension, (d) erectile dysfunction, (e) benign prostate hyperplasia, (f) female sexual disorders, (g) premature labor, (h) dysmenorrhea, (i) irritable bowl syndrome, (j) airway hyperactivity, (k) epilepsy, (l) stroke, (m) ischemia, (n) Alzheimer's disease, (o) Parkinson's diseases, (p) myocardial injury, (q) coronary artery disease, (r) angina, (s) pain, (t) eating disorders, (u) hair loss, (v) alopecia and (w) baldness, in a subject in need thereof.

DETAILED DESCRIPTION OF THE INVENTION

The present invention is directed to compounds of formula (I) and compounds of formula (II)

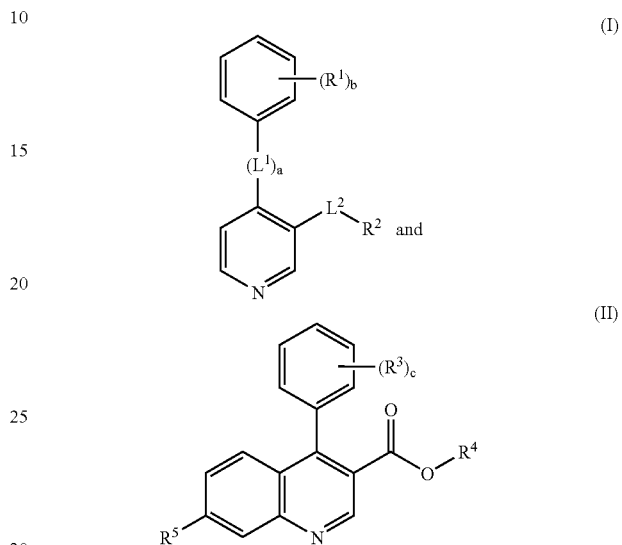

wherein a, $L^1$, b, $R^1$, $L^2$, $R^2$, c, $R^3$, $R^4$ and $R^5$ are as herein defined. The compounds of the present invention are to ion channels openers, more specifically, potassium channels openers, more specifically ATP-sensitive potassium channel openers. The compounds of the present are thus useful for treatment of various disorders including, but not limited to, urinary incontinence, overactive bladder, hypertension, erectile dysfunction, benign prostate hyperplasia, female sexual disorders, premature labor, dysmenorrhea, irritable bowl syndrome, airway hyperactivity, epilepsy, stroke, ischemia, Alzheimer's disease, Parkinson's diseases, myocardial injury, coronary artery disease, angina, pain, eating disorders, hair loss, alopecia and baldness. Preferably, the compounds of the present invention are useful in the treatment of urinary incontinence or overactive bladder.

In an embodiment of the present invention, a is 0. In another embodiment of the present invention a is 1. In an embodiment of the present invention b is 0. In another embodiment of the present invention b is an integer from 1 to 2.

In an embodiment of the present invention, $L^1$ is selected from the group consisting of —C(O)— and —CH(OH)—. Preferably, $L^1$ is —C(O)—.

In an embodiment of the present invention, $R^1$ is selected from the group consisting of halogen, $C_{1-4}$alkyl, hydroxy substituted $C_{1-4}$alkyl, halogenated $C_{1-4}$alkyl, $C_{1-4}$alkoxy, cyano, formyl and phenyl. In another embodiment of the present invention, $R^1$ is selected from the group consisting of hydroxy substituted $C_{1-4}$alkyl, cyano, $C_{1-4}$alkoxy and formyl. In another embodiment of the present invention, $R^1$ is selected from the group consisting of hydroxymethyl-, cyano, methoxy and formyl. Preferably, $R^1$ is cyano.

In an embodiment of the present invention, $L^2$ is selected from the group consisting of —C(O)—, —CH(OH)— and —CH₂—. Preferably, $L^2$ is —CH(OH)—.

In an embodiment of the present invention, $R^2$ is selected from the group consisting of hydrogen, hydroxy, $C_{1-4}$alkyl, trifluoromethyl, phenyl and t-butyl-dimethyl-silyloxy; wherein the phenyl is optionally substituted with one to three substituents independently selected from halogen, $C_{1-4}$alkyl, $C_{1-4}$alkoxy, $C_{1-4}$alkylthio-, amino, $C_{1-4}$alkylamino and di($C_{1-4}$alkyl)amino.

In another embodiment of the present invention, $R^2$ is selected from the group consisting of hydrogen, hydroxy, $C_{1-4}$alkyl, trifluoromethyl, phenyl and t-butyl-dimethyl-silyloxy; wherein the phenyl is optionally substituted with one to three substituents independently selected from halogen, $C_{1-4}$alkyl, $C_{1-4}$alkoxy, $C_{1-4}$alkylthio-, amino, $C_{1-4}$alkylamino and di($C_{1-4}$alkyl)amino.

In another embodiment of the present invention, $R^2$ is selected from the group consisting of hydrogen, hydroxy, methyl, trifluoromethyl, phenyl, 3-fluorophenyl, 4-fluorophenyl, 4-chlorophenyl, 3,4-dichlorophenyl, 2-methylphenyl, 4-methylphenyl, 2,4,6-trimethylphenyl, 4-t-butylphenyl, 2-methoxyphenyl, 3-methoxyphenyl, 4-methoxyphenyl, 2,5-dimethoxy-phenyl, 2,6-dimethoxyphenyl, 4-methylthiophenyl, dimethylamino-phenyl, 3-fluoro-4-methyl-phenyl, 3-fluoro-4-methoxy-phenyl, 2-methyl-5-fluoro-phenyl and t-butyl-dimethyl-silyloxy.

Preferably, $R^2$ is selected from the group consisting of trifluoromethyl, phenyl, 3-fluorophenyl, 4-chlorophenyl, 3,4-dichlorophenyl, 3,5-dichlorophenyl, 2-methylphenyl, 4-methylphenyl, 4-t-butylphenyl, 2-methoxyphenyl, 3-methoxyphenyl, 2,5-dimethoxyphenyl and 3-fluoro-4-methoxyphenyl. More preferably, $R^2$ is selected from the group consisting of phenyl, 3-fluorophenyl, 3,5-dichlorophenyl, 4-methylphenyl and 3-fluoro-4-methoxy-phenyl.

In an embodiment, the present invention is directed to compounds of formula (Ir)

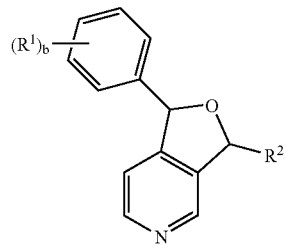

(Ir)

wherein c, $R^1$ and $R^2$ are as herein defined, and pharmaceutically acceptable salts thereof.

In an embodiment of the present invention, $L^1$ and $L^2$ are taken together to form a 5-membered, oxygen containing ring. In another embodiment of the present invention, $L^1$ and $L^2$ are taken together to form a 5-membered, oxygen containing ring, b is an integer from 0 to 1; $R^1$ is cyano; and $R^2$ is selected from the group consisting of hydrogen and hydroxy.

In an embodiment, the present invention is directed to a compound selected from the group consisting of 1-phenyl-1,3-dihydro-furo[3,4-c]pyridin-3-ol; 3-(1,3-dihydro-furo[3,4-c]pyridin-1-yl)-benzonitrile; 3-(3-hydroxy-1,3-dihydro-furo[3,4-c]pyridin-1-yl)-benzonitrile; and pharmaceutically acceptable salts thereof. In another embodiment, the present invention is directed to 3-(1,3-dihydro-furo[3,4-c]pyridin-1-yl)-benzonitrile, and pharmaceutically acceptable salts thereof.

In an embodiment of the present invention, $R^3$ is selected from the group consisting of halogen, cyano, $C_{1-4}$alkyl, $C_{1-4}$alkoxy, halogenated $C_{1-4}$alkyl, hydroxy substituted $C_{1-4}$alkyl, $C_{1-4}$alkyl-carbonyl-, $C_{1-4}$alkoxy-carbonyl-, formyl and phenyl. Preferably, $R^3$ is selected from the group consisting of fluoro, cyano, methyl, methoxy, trifluoromethyl, hydroxy-methyl-, methyl-carbonyl-, ethoxy-carbonyl-, formyl and phenyl.

In an embodiment of the present invention, $R^4$ is selected from the group consisting of $C_{1-4}$alkyl. Preferably, $R^4$ is ethyl.

In an embodiment of the present invention, $R^5$ is trifluoromethyl;

In an embodiment, the present invention is directed to a compound of formula (II) selected from the group consisting of 4-(5-formyl-2-methoxy-phenyl)-7-trifluoromethyl-quinoline-3-carboxylic acid ethyl ester; 4-(5-hydroxymethyl-2-methoxy-phenyl)-7-trifluoromethyl-quinoline-3-carboxylic acid ethyl ester; and pharmaceutically acceptable salts thereof.

In another embodiment of the present invention is any single compound or subset of compounds selected from the representative compounds listed in Tables 1-6 below.

Additional embodiments of the present invention, include those wherein the substituents selected for one or more of the variables defined herein (i.e. a, $L^1$, b, $R^1$, $L^2$, $R^2$, $R^3$, $R^4$ and $R^5$) are independently selected to be any individual substituent or any subset of substituents selected from the complete list as defined herein.

Representative compounds of the present invention are as listed in Table 1 to 5 below. Unless otherwise noted, wherein a stereogenic center is present in the listed compound, the compound was prepared as a mixture of stereo-configurations. Where a stereogenic center is present, the S* and R* designations are intended to indicate that the exact stereo-configuration of the center has not been determined.

TABLE 1

Compounds of Formula (II)

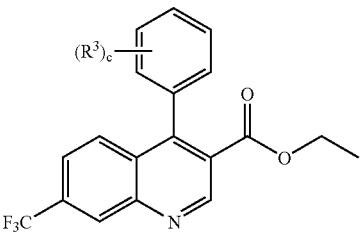

| ID No. | b | $R^1$ |
|---|---|---|
| 1 | 1 | 3-cyano |
| 2 | 2 | 3-methyl-5-methoxy |
| 3 | 2 | 3,5-di-trifluoromethyl |
| 4 | 1 | 4-ethoxy-carbonyl |
| 5 | 1 | 4-phenyl |
| 6 | 0 | — |
| 7 | 1 | 3-methyl-carbonyl |
| 8 | 2 | 2-fluoro-5-trifluoromethyl |
| 9 | 2 | 2-methoxy-5-formyl |
| 10 | 1 | 3-trifluoromethyl |
| 11 | 1 | 3-formyl |
| 12 | 1 | 3-hydroxy-methyl |
| 13 | 2 | 3,4-dimethyl |
| 14 | 2 | 2-methoxy-5-hydroxy-methyl |

TABLE 2

Compounds of Formula (I)

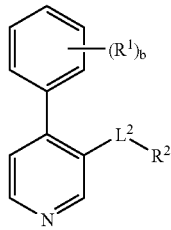

| ID No. | b | R¹ | L² | R² |
|---|---|---|---|---|
| 19 | 1 | 3-cyano | CH(OH) | phenyl |
| 20 | 1 | 3-cyano | CH(OH) | 4-fluoro-phenyl |
| 21 | 1 | 3-cyano | CH(OH) | 3-fluoro-phenyl |
| 22 | 1 | 3-cyano | CH(OH) | 3-fluoro-4-methyl-phenyl |
| 23 | 1 | 3-cyano | CH(OH) | 3,4-dichloro-phenyl |
| 24 | 1 | 3-cyano | CH(OH) | 3,4-dichloro-phenyl |
| 25 | 1 | 3-cyano | CH(OH) | 3,5-dichloro-phenyl |
| 26 | 1 | 3-cyano | CH(OH) | 4-chloro-phenyl |
| 27 | 1 | 3-cyano | CH(OH) | 4-t-butyl-phenyl |
| 28 | 1 | 3-cyano | CH(OH) | 2-methoxy-phenyl |
| 29 | 1 | 3-cyano | CH(OH) | 3-methoxy-phenyl |
| 30 | 1 | 3-cyano | CH(OH) | 4-methoxy-phenyl |
| 31 | 1 | 3-cyano | CH(OH) | 2-methyl-phenyl |
| 32 | 1 | 3-cyano | CH(OH) | 4-methyl-phenyl |
| 33 | 1 | 3-cyano | CH(OH) | 2,6-dimethoxy-phenyl |
| 34 | 1 | 3-cyano | CH(OH) | 4-methyl-thio-phenyl |
| 35 | 1 | 3-cyano | CH(OH) | 2,4,6-trimethyl-phenyl |
| 36 | 1 | 3-cyano | CH(OH) | 3-fluoro-4-methoxy-phenyl |
| 37 | 1 | 3-cyano | CH(OH) | 3-fluoro-4-methoxy-phenyl |
| 38 | 1 | 3-cyano | CH(OH) | 2-methyl-5-fluoro-phenyl |
| 39 | 1 | 3-cyano | CH(OH) | trifluoro-methyl |
| 40 | 2 | 2-methoxy-5-formyl | CH₂ | t-butyl-dimethyl-silyloxy |
| 41 | 2 | 2-methoxy-5-hydroxy-methyl | CH₂ | t-butyl-dimethyl-silyloxy |

TABLE 3

Compounds of Formula (I)

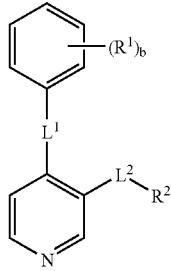

| ID No. | L¹ | b | R¹ | L² | R² |
|---|---|---|---|---|---|
| 42 | CH(OH) | 1 | 3-cyano | CH(OH) | phenyl |
| 43 | C(O) | 0 | — | CH(OH) | phenyl |
| 44 | C(O) | 0 | — | CH(OH) | 4-dimethyl-amino-phenyl |
| 45 | C(O) | 0 | — | CH(OH) | 3-fluoro-4-methoxy-phenyl |
| 46 | C(O) | 0 | — | CH(OH) | 2,5-dimethoxy-phenyl |
| 47 | C(O) | 0 | — | CH(OH) | 3-fluoro-phenyl |
| 48 | C(O) | 1 | 3-cyano | CH(OH) | phenyl |

TABLE 4

Compounds of Formula (I)

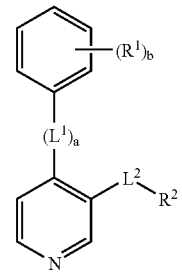

| ID No | (L¹)ₐ | (R¹)ᵦ | L² | R² |
|---|---|---|---|---|
| 50 | a = 0 | 3-cyano | —CH(OH)— | H |
| 51 | a = 0 | 3-cyano | —C(O)— | H |
| 52 | a = 0 | 3-cyano | —CH(OH)— | methyl |
| 53 | a = 0 | 2-methoxy-5-formyl | —C(O)— | H |
| 54 | a = 0 | 2-methoxy-5-formyl | —CH(OH)— | H |
| 56 | —CH(OH)— | b = 0 | —CH(OH)— | H |
| 57 | —CH(OH)— | 3-cyano | —CH(OH)— | H |
| 58 | a = 0 | 2-methoxy-5-hydroxy-methyl | —CH(OH)— | H |
| 59 | —C(O)— | b = 0 | —CH(OH)— | methyl |

TABLE 5

Compounds of Formula (Ir)

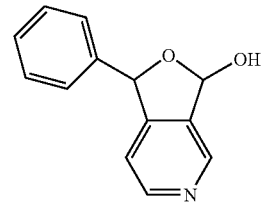

ID #65

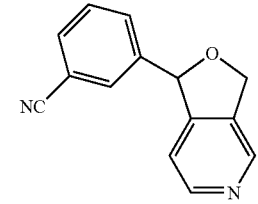

ID #66

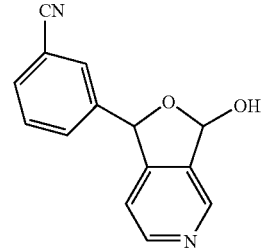

ID #55

Additional compounds, for example intermediates in the preparation of the compounds of the present invention, are as listed in Table 6 below.

TABLE 6

ID #15
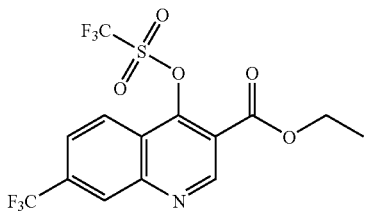

ID #49
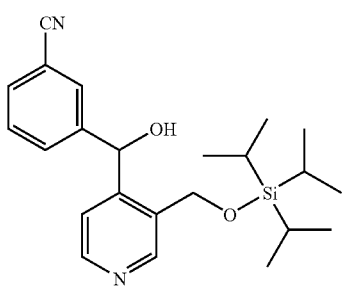

ID #60
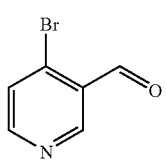

ID #61
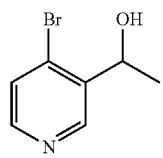

ID #62
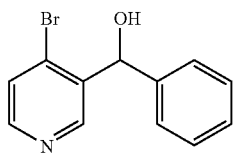

ID #63
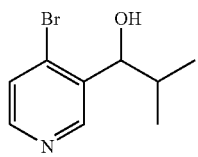

ID #64
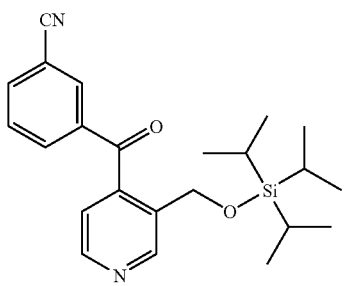

TABLE 6-continued

ID #68
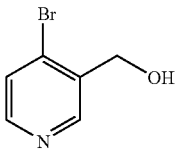

As used herein, "halogen" shall mean chlorine, bromine, fluorine and iodine, preferably fluorine or chlorine, more preferably fluorine.

As used herein, unless otherwise noted, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Similarly, the term "$C_{1-4}$alkyl" whether used alone or as part of a substituent group, include straight and branched chains containing 4 carbon atoms. For example, methyl, ethyl, n-propyl, isopropyl, n-butyl, isobutyl, sec-butyl and t-butyl.

As used herein, unless otherwise noted, the term "halogenated alkyl" shall mean any alkyl group as defined above substituted with at least one halogen atom, preferably substituted with a least one fluoro atom. Suitable examples include, but are not limited to, —$CF_3$, —$CH_2$—$CF_3$, —$CF_2$—$CF_2$—$CF_2$—$CF_3$, and the like. Similarly, the term "fluorinated alkyl" shall mean any alkyl group as defined above substituted with at least one fluorine atom, preferably substituted with one to three fluorine atoms.

As used herein, unless otherwise noted, the term "hydroxy substituted alkyl" shall mean alkyl group as defined above substituted with at least one hydroxy group. Preferably, the alkyl group is substituted with one hydroxy group. Preferably, the alkyl group is substituted with a hydroxy group at the terminal carbon. Suitable examples include, but are not limited to, —$CH_2(OH)$, —$CH_2$—$CH_2(OH)$, —$CH_2$—$CH(OH)$—$CH_2$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocylic aromatic groups such as phenyl, naphthyl, and the like.

As used herein, the notation "*" shall denote the presence of a stereogenic center.

When a particular group is "substituted" (e.g., alkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-$C_1$-$C_6$alkyl-aminocarbonyl-$C_1$-$C_6$alkyl-" substituent refers to a group of the formula

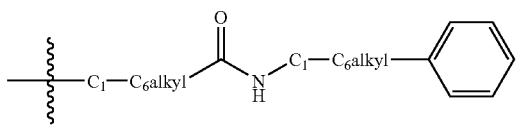

Abbreviations used in the specification, particularly the Schemes and Examples, are as follows:

| | |
|---|---|
| DCM = | Dichloromethane |
| DMEM = | Dulbecco's Modified Eagle's Medium |
| DMF = | N,N-Dimethylformamide |
| HEPES = | 4-(2-Hydroxyethyl)-1-Piperizine Ethane Sulfonic Acid |
| OAB = | Overactive bladder |
| Pd(PPh$_3$)$_4$ = | Tetrakistriphenylphosphine palladium (0) |
| Tf = | —SO$_2$—CF$_3$ |
| TFA = | Trifluoroacetic Acid |
| THF = | Tetrahydrofuran |
| UI = | Urinary Incontinence |

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of,the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will recognize that wherein a reaction step of the present invention may be carried out in a variety of solvents or solvent systems, said reaction step may also be carried out in a mixture of the suitable solvents or solvent systems.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycoilylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) wherein a is 0 (L¹ is absent) and L² is —CH(OH)— and R² is other than hydrogen may be prepared according to the process outlined in Scheme 1.

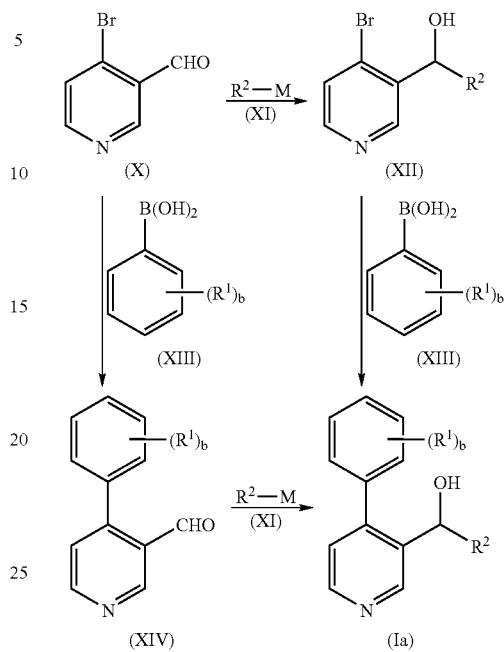

Scheme 1

Accordingly, a suitably substituted compound of formula (X), a known compound or compound prepared by known methods, is reacted with a suitably substituted compound of formula (XI), wherein M is MgCl, MgBr, Ml or Li, a known compound or compound prepared by known methods, in an organic solvent such as THF, diethyl ether, dioxane, and the like, to yield the corresponding compound of formula (XII).

The compound of formula (XII) is reacted with a suitably substituted compound of formula (XIII), a known compound or compound prepared by known methods, in the presence of a catalyst such as $Pd(PPh_3)_4$, $Pd(CH_3CN)_2Cl$, and the like, in the presence of a base such as $NaHCO_3$, $K_3PO_4$, $Na_2CO_3$, $K_2CO_3$, and the like, in an organic solvent such as toluene, dioxane, DMF, water, and the like, to yield the corresponding compound of formula (Ia).

Alternatively, a suitably substituted compound of formula (X), a known compound or compound prepared by known methods, is reacted with a suitably substituted compound of formula (XIII), a known compound or compound prepared by known methods, in the presence of a catalyst such as $Pd(PPh_3)_4$, $Pd(CH_3CN)_2Cl$, and the like, in the presence of a base such as $NaHCO_3$, $K_3PO_4$, $Na_2CO_3$, $K_2CO_3$, and the like, in an organic solvent such as toluene, dioxane, DMF, water, and the like, to yield the corresponding compound of formula (XIV).

The compound of formula (XIV) is reacted with a suitably substituted compound of formula (XI), wherein M is MgCl, MgBr, Ml or Li, a known compound or compound prepared by known methods, in an organic solvent such as THF, diethyl ether, dioxane, and the like, to yield the corresponding compound of formula (Ia).

One skilled in the art will recognize that the compound of formula (Ia) may be further, optionally, oxidized, according to known methods, to yield the corresponding compound of formula (I) wherein L² is —C(O)—. Alternatively, the compound of formula (Ia) may be further, optionally, reduced, according to known methods, to yield the corresponding compound of formula (I) wherein $L^2$ is —$CH_2$—.

Compounds of formula (I) wherein a is 1, $L^1$ is —CH(OH)— and $L^2$ is —CH(OH)— or $L^1$ and $L^2$ are taken together to form a 5-membered, oxygen containing ring may be prepared according to the process outlined in Scheme 2.

Compounds of formula (I) wherein a is 1, $L^1$ is —CH(OH)— and $L^2$ is —CH(OH)— may alternatively be prepared according to the process outlined in Scheme 3.

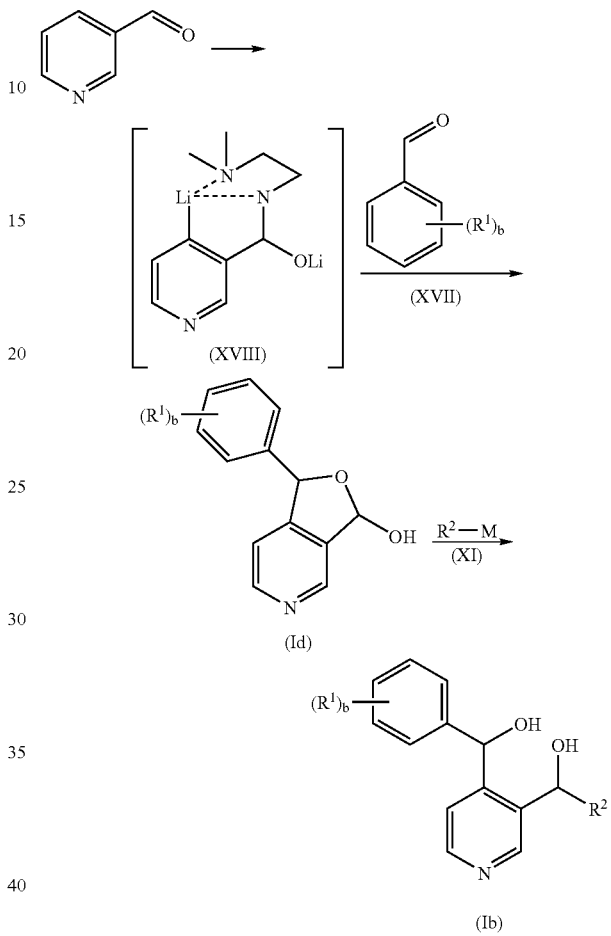

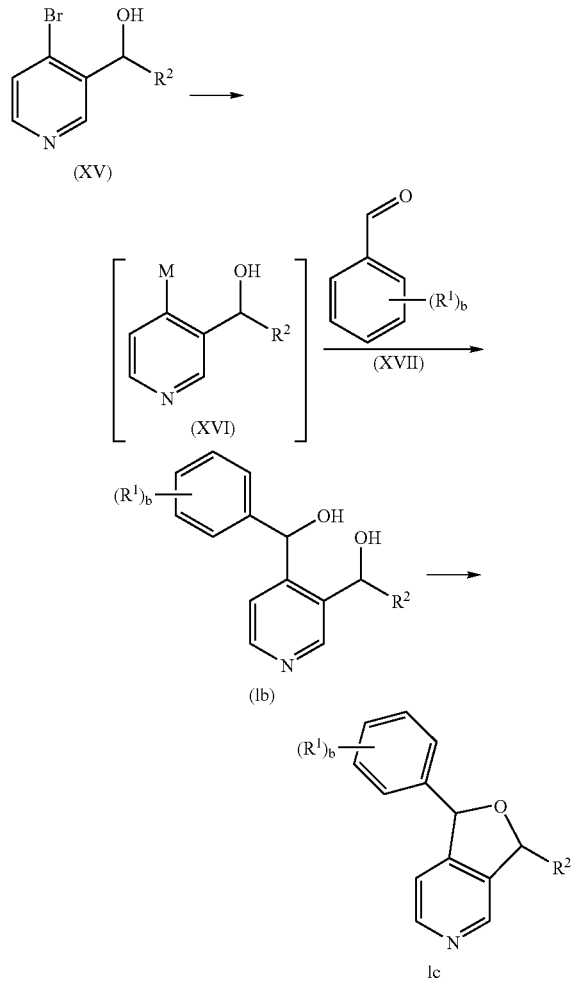

Accordingly, a suitably substituted compound of formula (XV), a known compound or compound prepared by known methods, is reacted with a suitable source of Mg or Li such as n-butyl lithium, isopropyl magnesium bromide, and the like, in an organic solvent such as THF, diethyl ether, dioxane, hexane, and the like, to yield the corresponding compound of formula (XVI), wherein M is Mg or Li. The compound of formula (XVI) is preferably not isolated.

The compound of formula (XVI) is reacted with a suitably substituted compound of formula (XVII), a known compound or compound prepared by known methods, in an organic solvent such as THF, diethyl ether, dioxane, hexane, and the like, to yield the corresponding compound of formula (Ib).

The compound of formula (Ib) is further, optionally reacted with a protic acid such as HCl, $H_2SO_4$, TFA, and the like, in an organic solvent such as THF, DCM, and the like, to yield the corresponding compound of formula (Ic).

Accordingly, pyridine-3-carbaldehyde, a known compound is reacted with $(CH_3)_2N$—$CH_2CH_2$—$NCH_3Li$, a known compound, at a temperature of about −78° C., then reacted with n-butyl lithium, in THF, and heated to about −42° C., for about 3 hours, to yield the compound of formula (XVIII). The compound of formula (XVIII) is preferably not isolated.

The compound of formula (XVIII) is reacted with a suitably substituted compound of formula (XVII), a known compound or compound prepared by known methods, in an organic solvent such as THF, dioxane, diethyl ether, and the like, to yield the corresponding compound of formula (Id).

The compound of formula (Id) is reacted with a suitably substituted compound of formula (XI), wherein M is MgCl, MgBr, MgI or Li, a known compound or compound prepared by known methods, in an organic solvent such as THF, dioxane, diethyl ether, and the like, to yield the corresponding compound of formula (Ib).

One skilled in the art will recognize that compounds of formula (I) wherein $L^1$ and $L^2$ are taken together to form a 5-membered oxygen containing ring and wherein $R^2$ is other than hydroxy may be prepared by reacting the corresponding compound of formula (Ib), according to known methods.

Compounds of formula (I) wherein a is 1, $L^1$ is —C(O)— and $L^2$ is —C(O)— may be prepared according to the process outlined in Scheme 4.

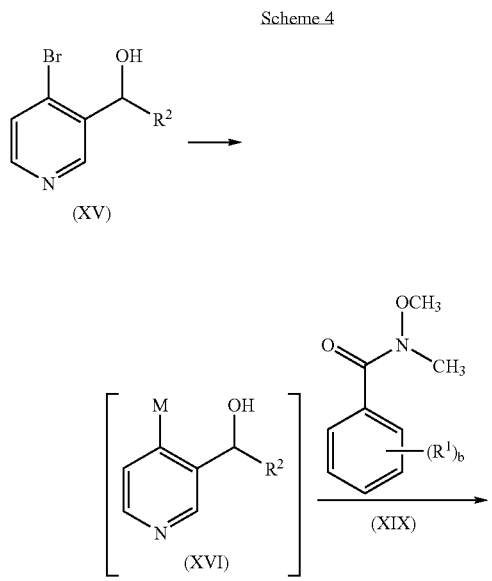

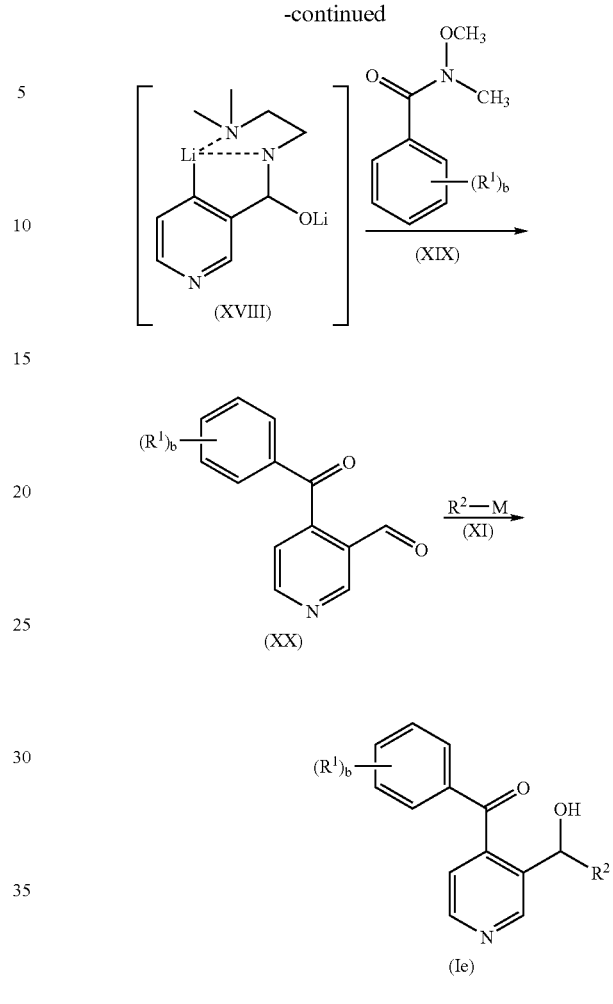

Accordingly, a suitably substituted compound of formula (XV), a known compound or compound prepared by known methods, is reacted with a suitable source of Mg or Li such as n-butyl lithium, isopropyl magnesium bromide, and the like, in an organic solvent such as THF, diethyl ether, dioxane, hexane, and the like, to yield the corresponding compound of formula (XVI), wherein M is Mg or Li. The compound of formula (XVI) is preferably not isolated.

The compound of formula (XVI) is reacted with a suitably substituted compound of formula (XIX), a known compound or compound prepared by known methods, in an organic solvent such as THF, dioxane, diethyl ether, hexane, and the like, to yield the corresponding compound of formula (Ie).

Compounds of formula (I) wherein a is 1, $L^1$ is —C(O)— and $L^2$ is —C(O)— may alternatively be prepared according to the process outlined in Scheme 5.

Scheme 5

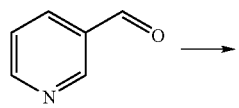

Accordingly, pyridine-3-carbaldehyde, a known compound is reacted with $(CH_3)_2N$—$CH_2CH_2$—$NCH_3Li$, a known compound, at a temperature of about –78° C., then reacted with n-butyl lithium, in THF, and heated to about –42° C., for about 3 hours, to yield the compound of formula (XVIII). The compound of formula (XVIII) is preferably not isolated.

The compound of formula (XVIII) is reacted with a suitably substituted compound of formula (XIX), a known compound or compound prepared by known methods, in an organic solvent such as THF, dioxane, diethyl ether, and the like, to yield the corresponding compound of formula (XX).

The compound of formula (XX) is reacted with a suitably substituted compound of formula (XI), wherein M is MgCl, MgBr, MgI or Li, a known compound or compound prepared by known methods, in an organic solvent such as THF, dioxane, diethyl ether, and the like, to yield the corresponding compound of formula (Ie).

One skilled in the art will recognize that compounds of formula (I) wherein $L^2$ is —C(O)— or —CH$_2$— may be prepared from the corresponding compound of formula (I) wherein $L^2$ is —CH(OH)— by oxidation or reduction, respectively, according to known methods.

Compounds of formula (II) may be prepared according to the process outlined in Scheme 6.

Scheme 6

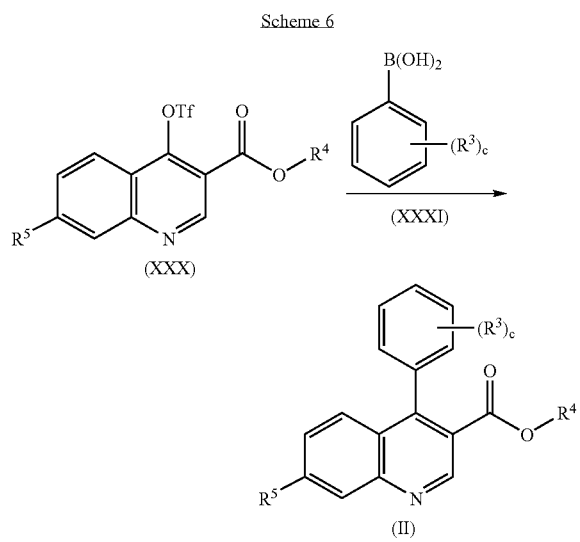

Accordingly, a suitably substituted compound of formula (XXX), a known compound or compound prepared by known methods, is reacted with a suitably substituted compound of formula (XXXI), a known compound or compound prepared by known methods, in the presence of a catalyst such as Pd(PPh$_3$)$_4$, Pd(CH$_3$CN)$_2$Cl, and the like, in the presence of a base such as NaHCO$_3$, K$_3$PO$_4$, Na$_2$CO$_3$, K$_2$CO$_3$, and the like, in an organic solvent such as toluene, dioxane, diethyl ether, and the like, to yield the corresponding compound of formula (II).

The present invention further comprises pharmaceutical compositions containing one or more compounds of formula (I) and/or compounds of formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01-500 mg and may be given at a dosage of from about 0.01-300 mg/kg/day, preferably from about 0.05-10.0 mg/kg/day, more preferably from about 0.05-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders related to ion channels, preferably a potassium ion channel, more preferably an ATP-sensitive potassium ion channels, described in the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders related to ion channels, preferably related to an potassium ion channel is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.05 to about 5.0 mg/kg of body weight per day, most preferably, from about 0.05 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products may be listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

4-Trifluoromethanesulfonyloxy-7-trifluoromethyl-quinoline-3-carboxylic acid ethyl ester (Compound #15)

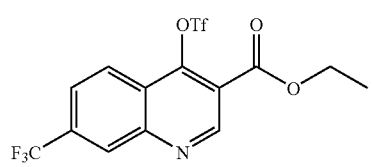

4-Hydroxy-7-trifluoromethyl-quinoline-3-carboxylic acid ethyl ester (2.85 g, 10 mmol) was suspended in the mixture of dichloromethane (50 mL) and pyridine (20 mL) at −20° C. The reaction mixture was then treated with trifluoromethanesulfonic anhydride (1.85 mL, 11 mmol). The reaction mixture was then allowed to warm to room temperature and stirred for 3 days. The reaction mixture was then diluted with ethyl acetate and washed saturated copper (II) sulfate solution, water (2×200 ml) and then brine. The organic layer was dried over sodium sulfate and concentrated to yield 4-trifluoromethanesulfonyloxy-7-trifluoromethyl-quinoline-3-carboxylic acid ethyl ester as a brown solid.

$^1$HNMR (DMSO-$d_6$, 300 MHz) δ (ppm) 9.78 (s, 1H), 9.06 (s, 1H), 8.11 (d, J=8.7 Hz, 1H), 7.72 (d, J=8.7 Hz, 1H), 4.20 (q, J=7.2 Hz, 2H), 1.09 (t, J=7.2 Hz, 3H);

LCMS: 2.585 min, m/z: 347.

EXAMPLE 2

4-(3-Cyano-phenyl)-7-trifluoromethyl-quinoline-3-carboxylic acid ethyl ester (Compound #1)

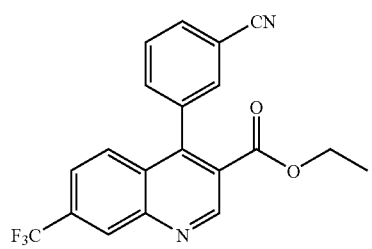

4-Trifluoromethanesulfonyloxy-7-trifluoromethyl-quinoline-3-carboxylic acid ethyl ester (417 mg, 1 mmol), 2-cyanophenylboronic acid (162 mg, 1.1 mmol), tetrakis(triphenylphosphine)palladium(0) (58 mg) and potassium phosphate (318 mg, 1.5 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(3-cyano-phenyl)-7-trifluoromethyl-quinoline-3-carboxylic acid ethyl ester as a white solid.

$^1$HNMR (CDCl$_3$, 300 MHz) δ (ppm) 9.52(s,1H), 8.53 (s,1H), 7.9-7.5 (m, 6H), 4.20 (q, J=7.2 Hz, 2H), 1.13 (t, J=7.2 Hz, 3H);

LCMS: 4.015 min, m/z: 371 (M+1).

EXAMPLE 3

4-Phenyl-7-trifluoromethyl-quinoline-3-carboxylic acid ethyl ester (Compound #6)

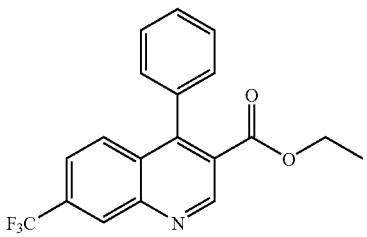

4-Trifluoromethanesulfonyloxy-7-trifluoromethyl-quinoline-3-carboxylic acid ethyl ester (208 mg, 0.5 mmol), phenylboronic acid (65 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-phenyl-7-trifluoromethyl-quinoline-3-carboxylic acid ethyl ester a colorless oil.

EXAMPLE 4

4-(3-Methoxy-5-methyl-phenyl)-7-trifluoromethyl-quinoline-3-carboxylic acid ethyl ester (Compound #2)

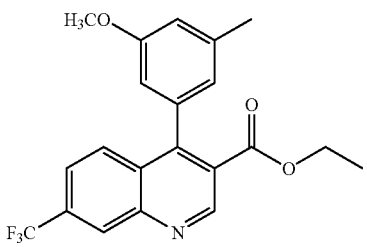

4-Trifluoromethanesulfonyloxy-7-trifluoromethyl-quinoline-3-carboxylic acid ethyl ester (208 mg, 0.5 mmol), 4-methyl-2-methoxyphenylboronic acid (92 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate and concentrated to yield a yellow oil which was purified by flash column eluted with 30% ethyl acetate in hexane, then recrystallization from ethyl ether to yield 4-(3-methoxy-5-methyl-phenyl)-7-trifluoromethyl-quinoline-3-carboxylic acid ethyl ester as a white powder.

$^1$HNMR (CDCl$_3$, 300 MHz) δ (ppm) 9.54 (s, 1H), 8.49 (s, 1H), 8.3-8.1 (m,2H), 8.08 (s, 1H), 7.77 (d, J=10.2 Hz, 1H), 6.98 (d, J=8.7 Hz, 1H), 4.32 (q, J=7.2 Hz, 2H), 3.97 (s, 3H), 2.29 (s, 3H), 1.19 (t, J=7.2 Hz, 3H);

LCMS: 4.091 min, m/z: 434.

EXAMPLE 5

4-(3,4-Dimethyl-phenyl)-7-trifluoromethyl-quinoline-3-carboxylic acid ethyl ester (Compound #13)

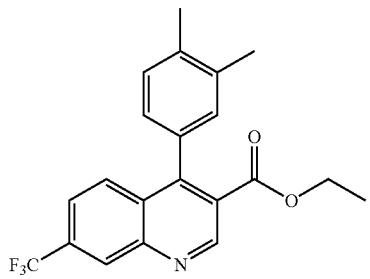

4-Trifluoromethanesulfonyloxy-7-trifluoromethyl-quinoline-3-carboxylic acid ethyl ester (208 mg, 0.5 mmol), 3,4-dimethylphenylboronic acid (82.5 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(3,4-dimethyl-phenyl)-7-trifluoromethyl-quinoline-3-carboxylic acid ethyl ester as a slight yellow oil.

LCMS: 4.115 min, m/z: 374 (M+1).

EXAMPLE 6

4-(3,5-Bis-trifluoromethyl-phenyl)-7-trifluoromethyl-quinoline-3-carboxylic acid-ethyl ester (Compound #3)

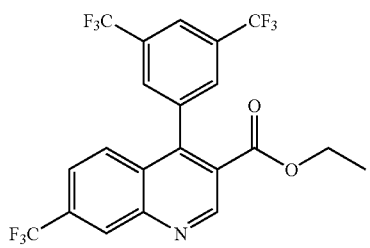

4-Trifluoromethanesulfonyloxy-7-trifluoromethyl-quinoline-3-carboxylic acid ethyl ester (208 mg, 0.5 mmol), 3,5-bis(trifluoromethyl)phenylboronic acid (142 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(3,5-bis-trifluoromethyl-phenyl)-7-trifluoromethyl-quinoline-3-carboxylic acid ethyl ester as a white solid.

EXAMPLE 7

4-(4-Ethoxycarbonyl-phenyl)-7-trifluoromethyl-quinoline-3-carboxylic acid ethyl ester (Compound #4)

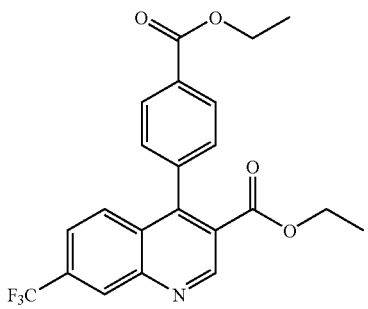

4-Trifluoromethanesulfonyloxy-7-trifluoromethyl-quinoline-3-carboxylic acid ethyl ester (208 mg, 0.5 mmol), 4-ethylcarboxylphenylboronic acid (107 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(4-ethoxycarbonyl-phenyl)-7-trifluoromethyl-quinoline-3-carboxylic acid ethyl ester as a yellow oil.

LCMS: 3.895 min, m/z: 418 (M+1).

EXAMPLE 8

4-Biphenyl-4-yl-7-trifluoromethyl-quinoline-3-carboxylic acid ethyl ester (Compound #5)

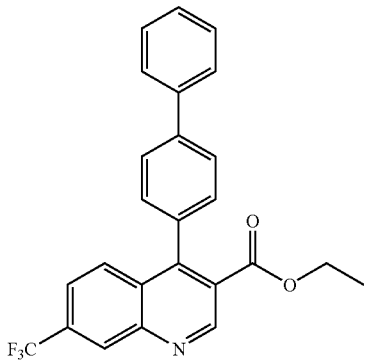

4-Trifluoromethanesulfonyloxy-7-trifluoromethyl-quinoline-3-carboxylic acid ethyl ester (208 mg, 0.5 mmol), 4-phenylphenylboronic acid (109 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice.

The organic layer was dried over sodium sulfate, concentrated, and the residue purified by flash column eluted with 30% ethyl acetate in hexane to yield 4-biphenyl-4-yl-7-trifluoromethyl-quinoline-3-carboxylic acid ethyl ester as a white solid.

LCMS: 4.177 min, m/z: 422 (M+1).

EXAMPLE 9

4-(3-Acetyl-phenyl)-7-trifluoromethyl-quinoline-3-carboxylic acid ethyl ester (Compound #7)

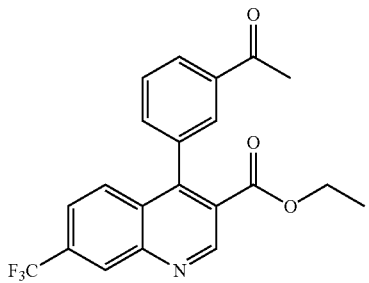

4-Trifluoromethanesulfonyloxy-7-trifluoromethyl-quinoline-3-carboxylic acid ethyl ester (208 mg, 0.5 mmol), 3-acetylphenylboronic acid (90 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(3-acetyl-phenyl)-7-trifluoromethyl-quinoline-3-carboxylic acid ethyl ester as a colorless oil.

LCMS: 3.894 min, m/z: 388 (M+1).

EXAMPLE 10

4-(2-Fluoro-5-trifluoromethyl-phenyl)-7-trifluoromethyl-quinoline-3-carboxylic acid ethyl ester (Comound #8)

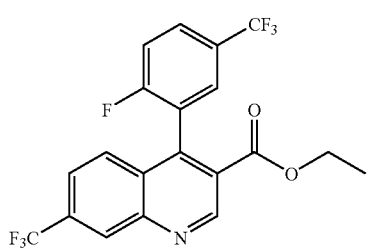

4-Trifluoromethanesulfonyloxy-7-trifluoromethyl-quinoline-3-carboxylic acid ethyl ester (208 mg, 0.5 mmol), 2-fluoro-5-trifluoromethylphenylboronic acid (142 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(2-fluoro-5-trifluoromethyl-phenyl)-7-trifluoromethyl-quinoline-3-carboxylic acid ethyl ester as a slight yellow oil.

LCMS: 4.308 min, m/z: 432 (M+1).

EXAMPLE 11

4-(5-Formyl-2-methoxy-phenyl)-7-trifluoromethyl-quinoline-3-carboxylic acid ethyl ester (Compound #9)

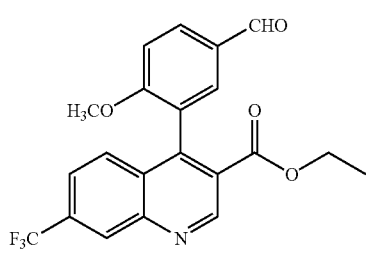

4-Trifluoromethanesulfonyloxy-7-trifluoromethyl-quinoline-3-carboxylic acid ethyl ester (208 mg, 0.5 mmol), 5-formal-2-methoxylphenylboronic acid (100 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(5-formyl-2-methoxy-phenyl)-7-trifluoromethyl-quinoline-3-carboxylic acid ethyl ester as a yellow solid.

LCMS: 3.361 min; m/z: 404 (M+1).

EXAMPLE 12

7-Trifluoromethyl-4-(3-trifluoromethyl-phenyl)-quinoline-3-carboxylic acid ethyl ester (Compound #10)

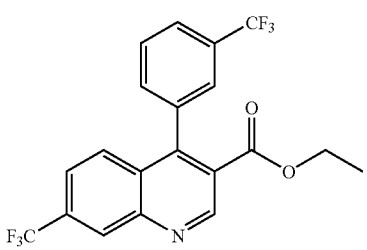

4-Trifluoromethanesulfonyloxy-7-trifluoromethyl-quinoline-3-carboxylic acid ethyl ester (208 mg, 0.5 mmol), 3-trifluoromethylphenylboronic acid (105 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 7-trifluoromethyl-4-(3-trifluoromethyl-phenyl)-quinoline-3-carboxylic acid ethyl ester as a white solid.

LCMS: 4.111 min, m/z: 414 (M+1).

EXAMPLE 13

4-(3-Formyl-phenyl)-7-trifluoromethyl-quinoline-3-carboxylic acid ethyl ester (Compound #11)

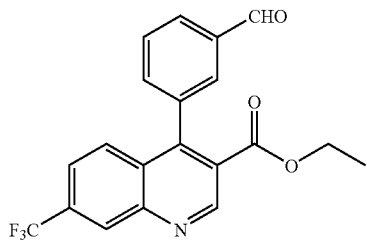

4-Trifluoromethanesulfonyloxy-7-trifluoromethyl-quinoline-3-carboxylic acid ethyl ester (208 mg, 0.5 mmol), 3-formalphenylboronic acid (82.5 mg, 0.55 mmol), tetrakis(triphenylphosphine)palladium(0) (29 mg) and potassium phosphate (159 mg, 0.75 mmol) were heated together in dioxane (5 mL) to 80° C. overnight. The reaction mixture was then diluted with ethyl acetate and washed with brine twice. The organic layer was dried over sodium sulfate, concentrated, and the residue purified by flash column eluted with 30% ethyl acetate in hexane to yield 4-(3-formyl-phenyl)-7-trifluoromethyl-quinoline-3-carboxylic acid ethyl ester as a white solid.

LCMS: 3.557 min, m/z: 374 (M+1).

EXAMPLE 14

4-(5-Hydroxymethyl-2-methoxy-phenyl)-7-trifluoromethyl-quinoline-3-carboxylic acid ethyl ester (Compound #14)

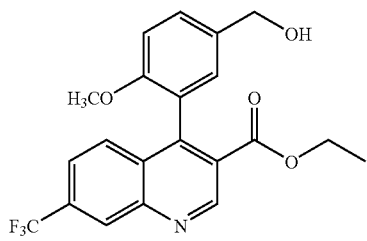

4-(5-Formyl-2-methoxy-phenyl)-7-trifluoromethyl-quinoline-3-carboxylic acid ethyl ester (30 mg, 0.074 mmol) was dissolved in ethanol (1 mL) and treated with sodium borohydride (26 mg) in one portion. After stirring at room temperature for 15 min, the reaction mixture was quenched with an aqueous solution of ammonium chloride. The reaction mixture was then extracted with ethyl acetate and the organic layer was dried over sodium sulfate, concentrated. The crude compound was purified by column chromatography eluted with 30% ethyl acetate to yield 4-(5-hydroxymethyl-2-methoxy-phenyl)-7-trifluoromethyl-quinoline-3-carboxylic acid ethyl ester as a white solid.

$^1$HNMR (CDCl$_3$, 300 MHz) δ (ppm) 9.46 (s, 1H), 8.48 (s, 1H), 7.7-7.4 (m, 3H), 7.13-7.03 (m, 2H), 4.71 (s, 2H), 4.17 (q, J=7.2 Hz, 2H), 3.68 (s, 3H), 1.09 (t, J=7.2 Hz, 3H);

LCMS: 3.175 min, m/z: 406 (M+1).

EXAMPLE 15

4-(3-Hydroxymethyl-phenyl)-7-trifluoromethyl-quinoline-3-carboxylic acid ethyl ester (Compound #12)

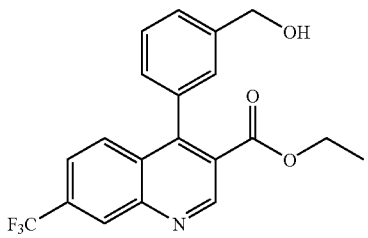

4-(3-Formyl-phenyl)-7-trifluoromethyl-quinoline-3-carboxylic acid ethyl ester (16 mg, 0.034 mmol) was dissolved in ethanol (1 mL) and treated with sodium borohydride (15 mg) in one portion. After stirring at room temperature for 15 min the reaction mixture was quenched with an aqueous solution of ammonium chloride. The reaction mixture was then extracted with ethyl acetate and the organic layer dried over sodium sulfate, concentrated and the residue purified by to column chromatography eluted with 30% ethyl acetate to yield 4-(3-hydroxymethyl-phenyl)-7-trifluoromethyl-quinoline-3-carboxylic acid ethyl ester as a yellow solid.

LCMS: 3.452 min, m/z: 376 (M+1).

EXAMPLE 16

4-Bromo-pyridine-3-carbaldehyde (Compound #60)

The title compound was prepared as described in *J. Org. Chem.* 1992, 57,1593-1597 and *Tetrahedron Letters,* 1999, 40, 4073-4076.

EXAMPLE 17

(4-Bromo-pyridin-3-yl)-methanol (Compound #68)

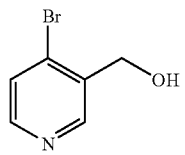

4-Bromo-pyridine-3-carbaldehyde (240 mg) in ethanol (10 mL) at 0° C. was treated with sodium borohydride (139 mg) for 30 min. The reaction mixture was then diluted with ethyl acetate and washed with aqueous ammonium chloride and brine to yield (4-bromo-pyridin-3-yl)-methanol as a white solid.

$^1$HNMR (CDCl$_3$, 300 MHz) δ (ppm): 10.4 (s, 1H), 9.01 (s, 1H), 8.56 (d, J=5.1 Hz, 1H), 7.63 (d, J=5.1 Hz, 1H).

EXAMPLE 18

3-(3-Hydroxymethyl-pyridin-4-yl)-benzonitrile (ID 50)

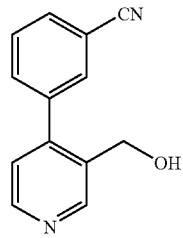

To a flask charged with (4-bromo-pyridin-3-yl)-methanol (90 mg, 0.48 mmol), 3-cyanophenylboronic acid (84.4 mg, 0.57 mmol) and tetrakis(triphenylphousphine)-palladium(0) (28 mg) was added 2 M Na$_2$CO$_3$ (2 mL) and toluene (3 mL). The reaction mixture was refluxed overnight and then extracted with ethyl acetate. The organic layer was dried over sodium sulfate and purified by column chromatography to yield 3-(3-Hydroxymethyl-pyridin-4-yl)-benzonitrile as a white solid.

$^1$HNMR (CDCl$_3$, 300 MHz) δ (ppm) 8.74 (s,1H), 8.60 (d, J=4.8 Hz,1H), 7.9-7.2 (m, 7H), 4.62 (s, 2H), 3.34 (bs, 1H);

LCMS: 2.815 min, m/z: 211 (M+1).

EXAMPLE 19

1-(4-Bromo-pyridin-3-yl)-ethanol (Compound #19)

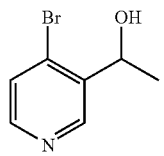

To a solution of 4-bromo-pyridine-3-carbaldehyde (400 mg, 2.15 mmol) in THF (10 mL) at −78° C. was added dropwise 3.0 M methylmagnesium bromide solution in THF (1.08 mL). After 15 min, the reaction mixture was quenched with saturated ammonium chloride solution and extracted with ethyl acetate, then purified by flash chromatography eluted with 50% ethyl acetate in hexane to yield 1-(4-bromo-pyridin-3-yl)-ethanol as white crystals.

$^1$HNMR (CDCl$_3$, 300 MHz) δ (ppm) 8.70 (s, 1H), 8.18 (d, J=5.1 Hz, 1H), 7.42 (d, J=5.1 Hz, 1H), 5.20 (q, J=6.6 Hz, 1H), 4.22 (bs, 1H), 1.51 (d, J=6.6 Hz, 3H);

LCMS: 1.275 min, m/z: 202 (M+1), 204 (M+3).

EXAMPLE 20

(4-Bromo-pyridin-3-yl)-phenyl-methanol (Compound #62)

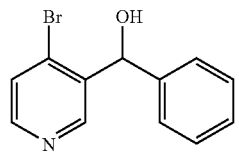

To a solution of 4-bromo-pyridine-3-carbaldehyde (400 mg, 2.15 mmol) in THF (10 mL) at −78° C. was added dropwise 3.0 M phenylmagnesium bromide solution in THF (1.08 mL). After 15 min, the reaction was quenched with saturated ammonium chloride solution and extracted with ethyl acetate, then purification by flash chromatography eluted with 50% ethyl acetate in hexane to yield (4-bromo-pyridin-3-yl)-phenyl-methanol as slight yellow crystals.

$^1$HNMR (DMSO-d$_6$, 300 MHz) δ (ppm) 8.74 (s, 1H), 8.31 (d, J=5.1 Hz, 1H), 7.65 (d, J =5.1 Hz, 1H), 7.4-7.2 (m, 5H), 6.30 (d, J=4.5 Hz, 1H), 5.96 (d, J=4.5 Hz, 1H);

LCMS: 1.893 min, m/z: 264 (M+1), 266 (M+3).

EXAMPLE 21

1-(4-Bromo-pyridin-3-yl)-2-methyl-propan-1-ol (Compoud #63)

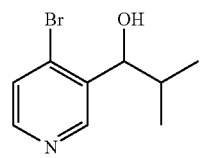

To a solution of 4-bromo-pyridine-3-carbaldehyde (400 mg, 2.15 mmol) in THF (10 mL) at −78° C. was added dropwise 1.0 M isopropyl-magnesium bromide solution in THF (3.23 mL). After 15 min, the reaction was quenched with saturated ammonium chloride solution and extracted with ethyl acetate, then purification by flash chromatography eluted with 50% ethyl acetate in hexane to yield 1-(4-bromo-pyridin-3-yl)-2-methyl-propan-1-ol as slight yellow crystals.

$^1$HNMR (CDCl$_3$, 300 MHz) δ (ppm) 8.60 (s,1H), 8.18 (d, J =5.4 Hz,1H), 7.43 (d, J=5.1 Hz, 1H), 4.85 (d, J=4.8 Hz, 1H), 3.46 (bs, 1H), 2.07 (m, 1H), 0.98 (d, J =2.4 Hz, 3H), 0.95 (d, J =2.4 Hz, 3H);

LCMS: 1.524 min, m/z: 230 (M+1), 232 (M+3).

EXAMPLE 22

3-(3-Formyl-pyridin-4-yl)-benzonitrile (Compound #51)

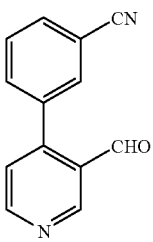

A flask was charged with 4-bromo-pyridine-3-carbaldehyde (186 mg, 1 mmol), 3-cyanophenelboronic acid (176 mg, 1.2 mmol), tetrakis(triphenylphosphine)palladium(0) (58 mg, 0.05 mmol), potassium phosphate (319 mg, 1.5 mmol) and 1,4-dioxane (10 mL). The reaction mixture was kept at 50° C. overnight. The reaction mixture was then diluted with ethyl acetate and washed with water, then brine. The organic layer was dried over sodium sulfate, concentrated, and the residue purified by flash chromatography to yield 3-(3-formyl-pyridin-4-yl)-benzonitrile as white crystals.

$^1$HNMR (CDCl$_3$, 300 MHz) δ (ppm) 10.1 (s, 1H), 9.20 (s,1H), 8.88 (d, J=5.1 Hz,1H), 7.9-7.6 (m, 4H), 7.36 (d, J=5.1 Hz, 1H);

MS: m/z: 209 (M+1), 227 (M+H$_2$O+1).

EXAMPLE 23

3-[3-(1-Hydroxy-ethyl)-pyridin-4-yl]-benzonitrile (Compound #52)

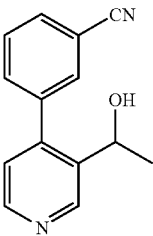

To a solution of 3-(3-formyl-pyridin-4-yl)-benzonitrile (30 mg) in THF (2 mL) at −78° C. was added 3.0 M methylmagnesium bromide in THF (0.144 mL). The reaction mixture was quenched with ammonium chloride and extracted with ethyl acetate. The organic layer was dried over sodium sulfate, concentrated, and the residue purified by flash chromatography to yield 3-[3-(1-hydroxy-ethyl)-pyridin-4-yl]-benzonitrile as a white foam.

$^1$HNMR (CDCl$_3$, 300 MHz) δ (ppm) 8.91 (s,1H), 8.53 (d, J=5.1 Hz,1H), 7.8- 7.5 (m, 4H), 7.10 (d, J=5.1 Hz,1H), 4.92 (m, 1H), 2.92 (bs, 1H), 1.471 (d, J=8.6 Hz, 3H);

LCMS: 2.968 min, m/z: 225 (M+1).

EXAMPLE 24

3-[3-(Hydroxy-phenyl-methyl)-pyridin-4-yl]-benzonitrile (Compound #19)

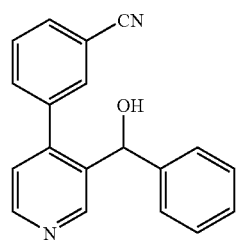

To a solution of 3-(3-formyl-pyridin-4-yl)-benzonitrile (21 mg, 0.1 mmol) in THF (1 mL) at −78° C. was added 3.0 M phenylmagnesium bromide in THF (0.1 mL). The reaction mixture was quenched with ammonium chloride and extracted with ethyl acetate. The organic layer was dried over sodium sulfate, concentrated, and the residue purified by flash chromatography to yield 3-[3-(hydroxy-phenyl-methyl)-pyridin-4-yl]-benzonitrile as a colorless oil.

$^1$HNMR (CDCl$_3$, 300 MHz) δ (ppm) 8.85 (s,1H), 8.52 (d, J=5.1 Hz, 1H), 7.7- 7.0 (m, 10H), 5.81 (d, J=3.6 Hz, 1H), 3.36 (d, J 3. Hz, 1H);

LCMS: 2.993 min, m/z: 287 (M+1)

EXAMPLE 25

4-(5-Formyl-2-methoxy-phenyl)-pyridine-3-carbaldehyde (Compound #53)

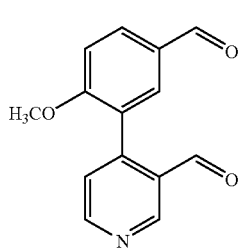

A flask was charged with 4-bromo-pyridine-3-carbaldehyde (93 mg, 0.5 mmol), 5-formal-2-methoxylphenelboronic acid (88 mg, 0.6 mmol), tetrakis(triphenylphosphine) palladium(0) (29 mg, 0.025 mmol), potassium phosphate (160 mg, 0.75 mmol) and 1,4-dioxane (5 mL). The reaction mixture was kept at 50° C. overnight. The reaction mixture was then diluted with ethyl acetate and washed with water then brine. The organic layer was dried over sodium sulfate, concentrated, and the residue purified by flash chromatography to yield 4-(5-formyl-2-methoxy-phenyl)-pyridine-3-carbaldehyde as a yellow solid.

LCMS: 1.16 min, m/z: 242 (M+1).

EXAMPLE 26

3-{3-[(4-Fluoro-phenyl)-hydroxy-methyl]-pyridin-4-yl}-benzonitrile (Compound #20)

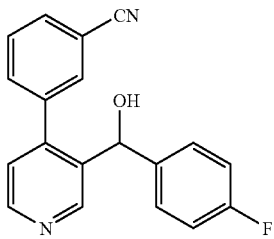

To a solution of 3-(3-formyl-pyridin-4-yl)-benzonitrile (50 mg, 0.24 mmol) in THF (2 mL) at −78° C. was added 1.0 M 4-fluorophenylmagnesium bromide in THF (0.5 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(4-fluoro-phenyl)-hydroxy-methyl]-pyridin-4-yl}-benzonitrile as a colorless oil.

LCMS: 2.207 min, m/z: 305 (M+1).

EXAMPLE 27

3-{3-[(3-Fluoro-phenyl)-hydroxy-methyl]-pyridin-4-yl}-benzonitrile (Compound #21)

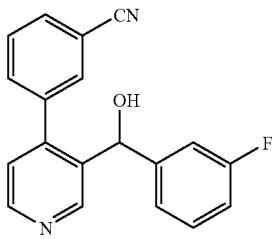

To a solution of 3-(3-formyl-pyridin-4-yl)-benzonitrile (41 mg, 0.20 mmol) in THF (2 mL) at −78° C. was added 1.0 M 3-fluorophenylmagnesium bromide in THF (0.4 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(3-fluoro-phenyl)-hydroxy-methyl]-pyridin-4-yl}-benzonitrile as a colorless oil.

LCMS: 2.517 min, m/z: 305 (M+1).

EXAMPLE 28

3-{3-[(3-Fluoro-4-methyl-phenyl)-hydroxy-methyl]-pyridin-4-yl}-benzonitrile (Compound #22)

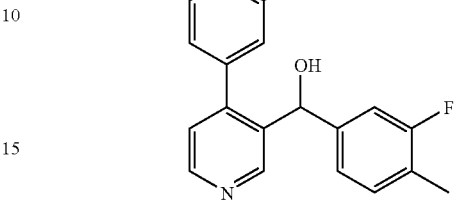

To a solution of 3-(3-formyl-pyridin-4-yl)-benzonitrile (41 mg, 0.20 mmol) in THF (2 mL) at −78° C. was added 0.5 M 3-fluoro-4-methylphenylmagnesium bromide in THF (0.8 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(3-fluoro-4-methyl-phenyl)-hydroxy-methyl]-pyridin-4-yl}-benzonitrile as a colorless oil.

$^1$HNMR (CDCl$_3$, 300 MHz) δ (ppm) 8.79 (s, 1H), 8.52 (d, J=5.1 Hz, 1H), 7.7-6.6 (m, 9H), 5.77 (s, 1H), 3.79 (bs, 1H), 2.22 (s, 3H);

LCMS: 2.358 min, m/z: 319 (M+1).

EXAMPLE 29

3-{3-[(3,4-Difluoro-phenyl)-hydroxy-methyl]-pyridin-4-yl}-benzonitrile (Compound #23)

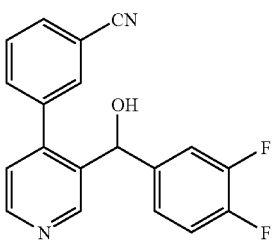

To a solution of 3-(3-formyl-pyridin-4-yl)-benzonitrile (30 mg, 0.15 mmol) in THF (1.5 mL) at −78° C. was added 0.5 M 3,4-difluorophenylmagnesium bromide in THF (0.6 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(3,4-difluoro-phenyl)-hydroxy-methyl]-pyridin-4-yl}-benzonitrile as white crystals.

$^1$HNMR (CDCl$_3$, 300 MHz) δ (ppm) 8.70 (s, 1H), 8.51 (d, J=5.1 Hz, 1H), 7.8-6.7 (m, 8H), 5.30(s, 1H), 4.33 (bs, 1H);

LCMS: 2.281 min, m/z: 323 (M+1).

EXAMPLE 30

3-{3-[(3,4-Dichloro-phenyl)-hydroxy-methyl]-pyridin-4-yl}-benzonitrile (Compound #24)

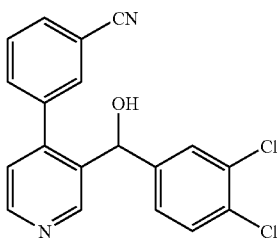

To a solution of 3-(3-formyl-pyridin-4-yl)-benzonitrile (30 mg, 0.15 mmol) in THF (1.5 mL) at −78° C. was added 0.5 M 3,4-dichlorophenylmagnesium bromide in THF (0.6 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(3,4-dichloro-phenyl)-hydroxy-methyl]-pyridin-4-yl}-benzonitrile as white crystals.

$^1$HNMR (CDCl$_3$, 300 MHz) δ (ppm) 8.69 (s, 1H), 8.53 (d, J=5.1 Hz, 1H), 7.8-6.8 (m, 8H), 5.80 (s, 1H), 4.15 (bs, 1H);

LCMS: 2.545 min, m/z: 355 (M+1).

EXAMPLE 31

3-{3-[(3,5-Dichloro-phenyl)-hydroxy-methyl]-pyridin-4-yl}-benzonitrile (Compound #25)

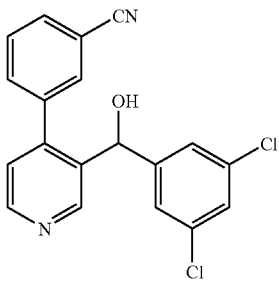

To a solution of 3-(3-formyl-pyridin-4-yl)-benzonitrile (30 mg, 0.15 mmol) in THF (1.5 mL) at −78° C. was added 0.5 M 3,5-dichlorophenylmagnesium bromide in THF (0.6 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(3,5-dichloro-phenyl)-hydroxy-methyl]-pyridin-4-yl}-benzonitrile as white crystals.

LCMS: 2.575 min, m/z: 355 (M+1).

EXAMPLE 32

3-{3-[(4-Chloro-phenyl)-hydroxy-methyl]-pyridin-4-yl}-benzonitrile (Copound #26)

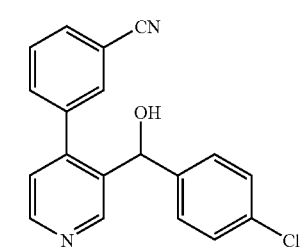

To a solution of 3-(3-formyl-pyridin-4-yl)-benzonitrile (30 mg, 0.15 mmol) in THF (1.5 mL) at −78° C. was added 0.5 M 4-chlorophenylmagnesium bromide in THF (0.6 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(4-chloro-phenyl)-hydroxy-methyl]-pyridin-4-yl}-benzonitrile as white crystals.

LCMS: 2.366 min, m/z: 321 (M+1).

EXAMPLE 33

3-{3-[(4-tert-Butyl-phenyl)-hydroxy-methyl]-pyridin-4-yl}-benzonitrile (Compound #27)

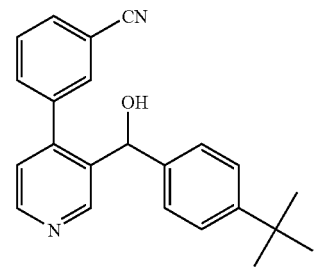

To a solution of 3-(3-formyl-pyridin-4-yl)-benzonitrile (30 mg, 0.15 mmol) in THF (1.5 mL) at −78° C. was added 2.0 M 4-tert-butylphenylmagnesium bromide in THF (0.15 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(4-tert-butyl-phenyl)-hydroxy-methyl]-pyridin-4-yl}-benzonitrile as a colorless oil.

$^1$HNMR (CDCl$_3$, 300 MHz) δ (ppm) 8.90 (s, 1H), 8.47 (d, J=5.1 Hz, 1H), 7.7-6.9 (m, 9H), 5.77 (s, 1H), 3.57 (bs, 1H), 1.30 (s, 9H);

LCMS: 2.733 min, m/z: 343 (M+1).

EXAMPLE 34

3-{3-[Hydroxy-(2-methoxy-phenyl)-methyl]-pyridin-4-yl}-benzonitrile (Compound #28)

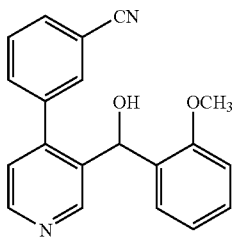

To a solution of 3-(3-formyl-pyridin-4-yl)-benzonitrile (30 mg, 0.15 mmol) in THF (1.5 mL) at −78° C. was added 1.0 M 2-methoxyphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(2-methoxy-phenyl)-methyl]-pyridin-4-yl}-benzonitrile as white crystals.

$^1$HNMR (CDCl$_3$, 300 MHz) δ (ppm) 8.79 (s,1H), 8.55 (d, J=5.1 Hz, 1H), 7.7-6.7 (m, 9H), 6.06 (s, 1H), 3.64 (s, 3H), 3.23 (bs, 1H);

LCMS: 2.467 min, m/z: 317 (M+1).

EXAMPLE 35

3-{3-[Hydroxy-(3-methoxy-phenyl)-methyl]-pyridin-4-yl}-benzonitrile (Compound #29)

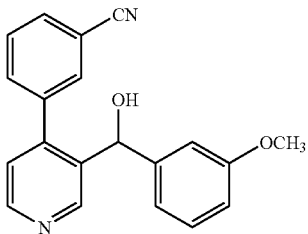

To a solution of 3-(3-formyl-pyridin-4-yl)-benzonitrile (30 mg, 0.15 mmol) in THF (1.5 mL) at −78° C. was added 1.0 M 3-methoxyphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(3-methoxy-phenyl)-methyl]-pyridin-4-yl}-benzonitrile as white crystals.

$^1$HNMR (CDCl$_3$, 300 MHz) δ (ppm) 8.78 (s,1H), 8.47 (d, J=5.1 Hz, 1H), 7.7-6.6 (m, 9H), 5.77 (s, 1H), 3.96 (bs, 1H), 3.73 (s, 3H);

LCMS: 2.433 min, m/z: 317 (M+1).

EXAMPLE 36

3-{3-[Hydroxy-(4-methoxy-phenyl)-methyl]-pyridin-4-yl}-benzonitrile (Compound #30)

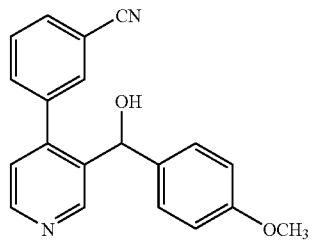

To the solution of 3-(3-formyl-pyridin-4-yl)-benzonitrile (30 mg, 0.15 mmol) in THF (1.5 mL) at −78° C. was added 0.5 M 4-methoxyphenylmagnesium bromide in THF (0.6 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(4-methoxy-phenyl)-methyl]-pyridin-4-yl}-benzonitrile as white crystals.

$^1$HNMR (CDCl$_3$, 300 MHz) δ (ppm) 8.88 (s, 1H), 8.49 (d, J=5.1 Hz, 1H), 7.7-6.7 (m, 9H), 5.74 (s, 1H), 3.77 (s, 3H), 3.68 (bs, 1H);

LCMS: 2.402 min, m/z: 317 (M+1).

EXAMPLE 37

3-{3-[Hydroxy-(2-methyl-phenyl)-methyl]-pyridin-4-yl}-benzonitrile (Compound #31)

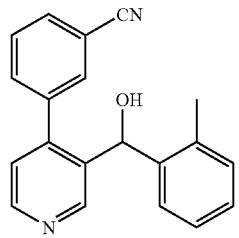

To a solution of 3-(3-formyl-pyridin-4-yl)-benzonitrile (30 mg, 0.15 mmol) in THF (1.5 mL) at −78° C. was added 2.0 M 2-methylphenylmagnesium bromide in THF (0.15 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(2-methyl-phenyl)-methyl]-pyridin-4-yl}-benzonitrile as white crystals.

$^1$HNMR (CDCl$_3$, 300 MHz) δ (ppm) 8.64 (s, 1H), 8.48 (d, J=5.1 Hz, 1H), 7.7-6.7 (m, 9H), 5.83 (s, 1H), 3.75 (s, 1H), 1.80 (s, 3H);

LCMS: 2.185 min, m/z: 301 (M+1).

EXAMPLE 38

3-{3-[Hydroxy-(4-methyl-phenyl)-methyl]-pyridin-4-yl}-benzonitrile (Comound #32)

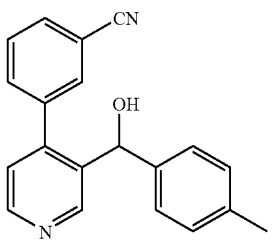

To a solution of 3-(3-formyl-pyridin-4-yl)-benzonitrile (15 mg, 0.075 mmol) in THF (1 mL) at −78° C. was added 0.5 M 4-methylphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(2-methyl-phenyl)-methyl]-pyridin-4-yl}-benzonitrile as white crystals.

LCMS: 2.282 min, m/z: 301 (M+1).

EXAMPLE 39

3-{3-[Hydroxy-(2,5-dimethoxy-phenyl)-methyl]-pyridin-4-yl}-benzonitrile (Compound #33)

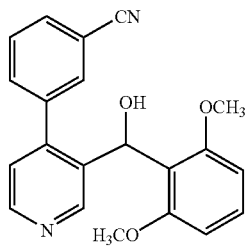

To a solution of 3-(3-formyl-pyridin-4-yl)-benzonitrile (15 mg, 0.075 mmol) in THF (1 mL) at −78° C. was added 0.5 M 2,5-dimethoxylphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(2,5-dimethoxy-phenyl)-methyl]-pyridin-4-yl}-benzonitrile as white crystals.

$^1$HNMR (CDCl$_3$, 300 MHz) δ (ppm) 8.77(s, 1H), 8.55 (d, J =3.9 Hz, 1H), 7.7-6.7 (m, 8H), 6.03 (s, 1H), 3.75 (s, 3H), 3.60(s, 3H), 3.40 (bs, 1H);

LCMS: 2.516 min, m/z: 347 (M+1).

EXAMPLE 40

3-{3-[(3-Fluoro-4-methoxy-phenyl)-hydroxy-methyl]-pyridin-4-yl}-benzonitrile (Compound #37)

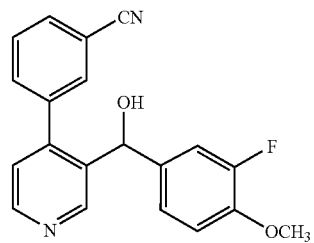

To a solution of 3-(3-formyl-pyridin-4-yl)-benzonitrile (15 mg, 0.075 mmol) in THF (1 mL) at −78° C. was added 0.5 M 3-fluoro-4-methoxyphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(3-fluoro-4-methoxy-phenyl)-hydroxy-methyl]-pyridin-4-yl}-benzonitrile as a colorless oil.

$^1$HNMR (CDCl$_3$, 300 MHz) δ (ppm) 8.81 (s, 1H), 8.54 (d, J=3.9 Hz, 1H), 7.8-6.6 (m, 8H), 5.76 (s, 1H), 3.87 (s, 3H), 3.66 (bs, 1H);

LCMS: 2.495 min, m/z: 335 (M+1).

EXAMPLE 41

3-{3-[(5-Fluoro-2-methyl-phenyl)-hydroxy-methyl]-pyridin-4-yl}-benzonitrile (Compound #38)

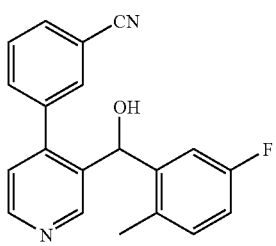

To a solution of 3-(3-formyl-pyridin-4-yl)-benzonitrile (15 mg, 0.075 mmol) in THF (1 mL) at −78° C. was added 0.5 M 3-fluoro-5-methylphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(5-fluoro-2-methyl-phenyl)-hydroxy-methyl]-pyridin-4-yl}-benzonitrile as white crystals.

$^1$HNMR (CDCl$_3$, 300 MHz) δ (ppm) 8.533 (s, 1H), 8.525 (s, 1H), 7.8-6.6 (m, 8H), 5.78 (s, 1H), 3.69 (bs, 1H), 1.73 (s, 3H);

LCMS: 2.547 min, m/z: 319 (M+1).

EXAMPLE 42

3-{3-[Hydroxy-(2,4,6-trimethyl-phenyl)-methyl]-pyridin-4-yl}-benzonitrile (Compound #35)

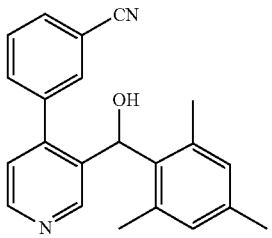

To a solution of 3-(3-formyl-pyridin-4-yl)-benzonitrile (15 mg, 0.075 mmol) in THF (1 mL) at −78° C. was added 0.5 M 2,4,6-trimethylphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(2,4,6-trimethyl-phenyl)-methyl]-pyridin-4-yl}-benzonitrile as white crystals.

$^1$HNMR (CDCl$_3$, 300 MHz) δ (ppm) 9.012 (s, 1H), 8.50 (d, J=4.8 Hz, 1H), 7.6-6.9 (m, 5H), 6.66 (s, 2H), 6.08 (s,1H), 2.73 (bs,1H), 2.24 (s, 3H), 1.91 (s, 6H);

LCMS: 2.417 min. m/z: 329 (M+1).

EXAMPLE 43

3-{3-[Hydroxy-(4-methylsulfanyl-phenyl)-methyl]-pyridin-4-yl}-benzonitrile (Compound #34)

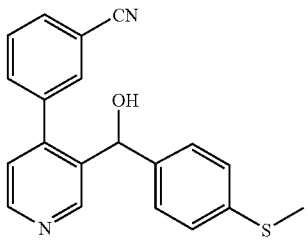

To a solution of 3-(3-formyl-pyridin-4-yl)-benzonitrile (15 mg, 0.075 mmol) in THF (1 mL) at −78° C. was added 0.5 M 4-methylsulfanylphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[hydroxy-(4-methylsulfanyl-phenyl)-methyl]-pyridin-4-yl}-benzonitrile as white crystals.

$^1$HNMR (CDCl$_3$, 300 MHz) δ (ppm) 8.814 (s, 1H), 8.50 (d, J=5.1 Hz, 1H), 7.7-6.6 (m, 9H), 5.76 (s, 1H), 3.71 (bs, 1H), 2.45 (s, 3H);

LCMS: 2.591 min. m/z: 333 (M+1).

EXAMPLE 44

3-{3-[(5-Fluoro-2-methoxy-phenyl)-hydroxy-methyl]-pyridin-4-yl}-benzonitrile (Compound #36)

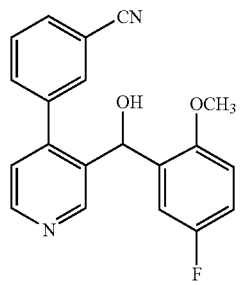

To a solution of 3-(3-formyl-pyridin-4-yl)-benzonitrile (15 mg, 0.075 mmol) in THF (1 mL) at −78° C. was added 0.5 M 3-fluoro-6-methoxyphenylmagnesium bromide in THF (0.3 mL). The reaction mixture was quenched with ammonium chloride and extracted with ethyl acetate. The organic layer was dried over sodium sulfate, concentrated, and the residue purified by flash chromatography eluted with 5% methanol in dichloromethane to yield 3-{3-[(5-fluoro-2-methoxy-phenyl)-hydroxy-methyl]-pyridin-4-yl}-benzonitrile as white crystals.

$^1$HNMR (CDCl$_3$, 300 MHz) δ (ppm) 8.75 (s, 1H), 8.61 (d, J=3.9 Hz, 1H), 7.8-6.6 (m, 8H), 6.04 (s, 1H), 3.63 (s, 3H), 2.07 (bs, 1H);

LCMS: 2.191 min, m/z: 335 (M+1).

EXAMPLE 45

3-[3-(2,2,2-Trifluoro-1-hydroxy-ethyl)-pyridin-4-yl]-benzonitrile (Compound #39)

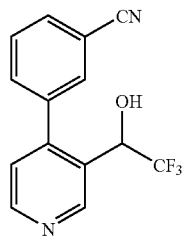

To a solution of 3-(3-formyl-pyridin-4-yl)-benzonitrile (31 mg, 0.15 mmol) and cesium fluoride (23 mg) in DMF (2 mL) at room temperature was added trimethyl-trifluoromethyl-silanein (0.44 mL). The reaction mixture was quenched with ammonium chloride and extracted with ethyl acetate. The organic layer was dried over sodium sulfate and concentrated, and the residue purified by flash chromatography eluted with 5% methanol in dichloromethane to yield 3-[3-(2,2,2-trifluoro-1-hydroxy-ethyl)-pyridin-4-yl]-benzonitrile as white crystals.

$^1$HNMR (CDCl$_3$, 300 MHz) δ (ppm) 8.92 (s, 1H), 8.59 (d, J=5.1 Hz, 1H), 7.8-7.2 (m, 5H), 5.64 (s, 1H), 5.09 (q, J=6.6 Hz, 1H);

LCMS: 2.519 min. m/z: 279 (M+1).

EXAMPLE 46

3-[Hydroxy-(3-hydroxymethyl-pyridin-4-yl)-methyl]-benzonitrile (Compound #57)

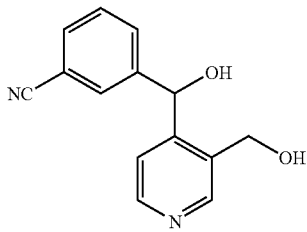

To a solution of (4-bromo-pyridin-3-yl)-methanol (20 mg, 0.11 mmol) in THF (1 mL) at −78° C. was added dropwise 2.5M n-butyllithium (0.22 mL). After 15 min, a solution of 3-cyanobenzaldehyde (69 mg) in THF (0.5 mL) was added. The reaction mixture was stirred for 15 min, then quenched with ammonium chloride solution and extracted with ethyl acetate. The organic layer was dried over sodium sulfate, concentrated, and the residue purified by flash chromatography to yield 3-[hydroxy-(3-hydroxymethyl-pyridin-4yl)-methyl]-benzonitrile as a white solid.

EXAMPLE 47

3-{Hydroxy-[3-(hydroxy-phenyl-methyl)-pyridin-4-yl]-methyl}-benzonitrile (Compound #42)

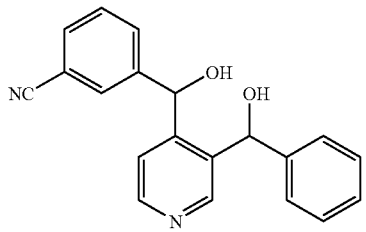

To a solution of (4-bromo-pyridin-3-yl)-methanol (53 mg 0.2 mmol) in THF (2 mL) at −78° C. was added dropwise 2.5 M n-butyllithium (0.24 mL, 0.6 mmol). After 15 min a solution of 3-cyanobenzaldehyde (79 mg) in THF (0.5 ml) was added. The reaction mixture was stirred for 15 min, then quenched with ammonium chloride solution and extracted with ethyl acetate. The organic layer was dried over sodium sulfate, concentrated and the residue purified by flash chromatography to yield 3-{hydroxy-[3-(hydroxy-phenyl-methyl)-pyridin-4-yl]-methyl}-benzonitrile as white crystals.

LCMS: 2.250 min, m/z: 317 (M+1).

EXAMPLE 48

3-(3-Hydroxymethyl-pyridin-4-yl)-4-methoxy-benzaldehyde (ID 54)

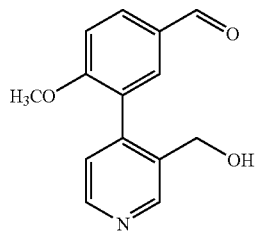

A flask was with charged 4-bromo-pyridine-3-carbaldehyde (376 mg, 2 mmol), 3-formal-6-methoxyphenelboronic acid (432 mg, 2.4 mmol), tetrakis(triphenylphosphine) palladium(0) (116 mg, 0.1 mmol), potassium phosphate (638 mg, 3 mmol) and 1,4-dioxane (20 mL). The reaction mixture was kept at 80° C. overnight, then diluted with ethyl acetate and washed with water then brine. The organic layer was dried over sodium sulfate, concentrated, and the residue purified by flash chromatography to yield 3-(3-hydroxymethyl-pyridin-4-yl)-4-methoxy-benzaldehyde as a yellow oil.

$^1$HNMR (CDCl$_3$, 300 MHz) δ (ppm) 9.90 (s, 1H), 8.76 (s, 1H), 8.50 (d, J=5.1 Hz, 1H), 7.95 (dd, $^1$J=8.4 Hz, $^2$J=2.1 Hz, 1H), 7.70 (d, J=2.1 Hz, 1H), 7.1 (m, 2H), 4.52 (s, 2H), 3.86 (s, 3H);

LCMS: 1.834 min, m/z: 244 (M+1).

EXAMPLE 49

3-[3-(tert-Butyl-dimethyl-silanyloxymethyl)-pyridin-4-yl]-4-methoxy-benzaldehyde (Compound #40)

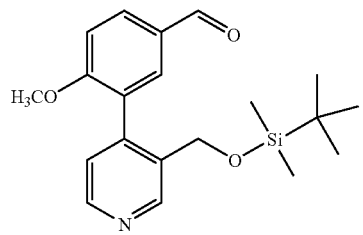

3-(3-Hydroxymethyl-pyridin-4-yl)-4-methoxy-benzaldehyde (240 mg, 1 mmol), tert-butylchlorodimethylsilane (226 mg), and imidazole (102 mg) were dissolved in DMF (2 mL) at room temperature and then stirred for 1 h. The reaction mixture was diluted with ethyl ether and washed with water three times, and then once with brine. The resulting product was purified by column chromatography to yield 3-[3-(tert-butyl-dimethyl-silanyloxymethyl)-pyridin-4-yl]-4-methoxy-benzaldehyde as a colorless oil.

$^1$HNMR (CDCl$_3$, 300 MHz) δ (ppm) 9.93 (s, 1H), 8.80 (s, 1H), 8.57 (d, J=4.8 Hz, 1H), 7.95 (dd, $^1$J=8.7 Hz, $^2$J=2.1 Hz, 1H), 7.71 (d, J=2.1 Hz, 1H), 7.11 (m, 2H), 4.53 (bs, 2H), 3.86 (s, 3H), 0.85 (s, 9H), −0.05 (s, 6H);

LCMS: 2.874 min, m/z: 358 (M+1).

EXAMPLE 50

{3-[3-(tert-Butyl-dimethyl-silanyloxymethyl)-pyridin-4-yl]-4-methoxy-phenyl}-methanol (Compound #41)

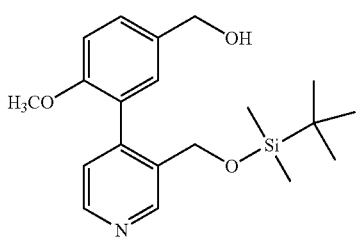

3-[3-(tert-Butyl-dimethyl-silanyloxymethyl)-pyridin-4-yl]-4-methoxy-benzaldehyde (160 mg) was dissolved into ethanol (3 mL) and treated with sodium borohydride (85 mg). The reaction mixture was stirred for 1 hour, diluted with ethyl acetate and washed with brine. The organic layer was dried over sodium sulfate, concentrated, and the residue purified by flash chromatography to yield {3-[3-(tert-butyl-dimethyl-silanyloxymethyl)-pyridin-4-yl]-4-methoxy-phenyl}-methanol as a colorless oil.

$^1$HNMR (CDCl$_3$, 300 MHz) δ (ppm) 8.80 (s,1H), 8.51 (d, J=4.8 Hz, 1H), 7.95 (dd, $^1$J=8.7 Hz, $^2$J=2.1 Hz, 1H), 7.71 (d, J=2.1 Hz, 1H), 7.10 (d, J=4.8 Hz, 1H), 6.98 (d, J=8.7 Hz, 1H), 4.70 (s, 2H), 4.59 (bs, 2H), 3.78 (s, 3H), 2.70 (bs, 1H), 0.89 (s, 9H), 0.00 (s, 6H);

LCMS: 2.752 min, m/z: 360 (M+1).

EXAMPLE 51

1-Phenyl-1,3-dihydro-furo[3,4-c]pyridin-3-ol (Compound #65)

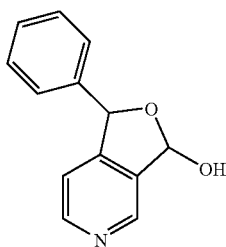

N,N,N'-trimethylethane (1.55 ml, 12 mmol) was dissolved in THF (30 mL) and cooled to −78° C. 2.5 M n-butyllithium (4.4 mL) was then added to the reaction mixture, which was then stirred for 15 min, before addition of pyridine-3-carbaldehyde (0.94 mL, 10 mmol). The reaction mixture was maintained at −78° C. for 15 min, then n-butyllithium (8 mL) was added slowly so that the temperature was always below −42° C. The reaction mixture was stirred for 1 hour at −42° C., then cooled to −78° C. Benzaldehyde (3 mL) was then added slowly into the reaction mixture, which was then stirred for 15 min. The reaction mixture was quenched with ammonium chloride and extracted with ethyl acetate. The organic layer was dried over sodium sulfate and purified by flash chromatography eluted with 5% methanol in dichloromethane to yield 1-phenyl-1,3-dihydro-furo[3,4-c]pyridin-3-ol as a yellow solid.

LCMS: 1.829 min, m/z: 214 (M+1).

EXAMPLE 52

3-(3-Hydroxy-1,3-dihydro-furo[3,4-c]pyridin-1-yl)-benzonitrile (Compound #55)

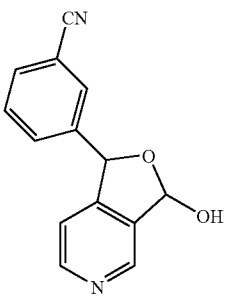

N,N,N'-trimethylethane (1.55 mL, 12 mmol) was dissolved in THF (30 mL) and cooled to −78° C. 2.5 M n-butyllithium (4.4 mL) was added into the reaction mixture, which was then stirred for 15 min, before the addition of pyridine-3-carbaldehyde (0.94 mL, 10 mmol). The reaction mixture was maintained at −78° C. for 15 min, then n-butyllithium (8 mL) was added slowly so that the temperature was always below −42° C. The reaction mixture was stirred 1 hour at 42° C., then cooled to −78° C. before it was transfer through a cannula into a solution of 3-cyanobenzaldehyde (23.9 g) in THF (5 mL) at −78° C., then stirred again for 15 min. The reaction mixture was then quenched with ammonium chloride aqueous solution and extracted with ethyl acetate. The organic layer was dried over sodium sulfate and purified by flash chromatography eluted with 5% methanol in dichloromethane to yield 3-[(3-formyl-pyridin-4-yl)-hydroxy-methyl]-benzonitrile as a yellow solid.

LCMS: 2.752 min, m/z: 239 (M+1).

EXAMPLE 53

(3-Hydroxymethyl-pyridin-4-yl)-phenyl-methanol (Compound #56)

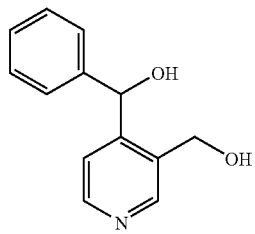

1-Phenyl-1,3-dihydro-furo[3,4-c]pyridin-3-ol (50 mg) was dissolved in ethanol (2 mL) and treated with sodium borohydride (13 mg). The reaction mixture was stirred for 1 hour and then diluted with ethyl acetate and washed with brine. The organic layer was dried over sodium sulfate, concentrated, and the residue purified by flash chromatography to yield (3-hydroxymethyl-pyridin-4-yl)-phenyl-methanol as a colorless foam.

LCMS: 0.614 min, m/z: 216 (M+1).

EXAMPLE 54

3-[Hydroxy-(3-hydroxymethyl-pyridin-4-yl)-methyl]-benzonitrile (Compound #57)

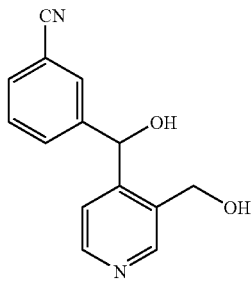

3-(3-Hydroxy-1,3-dihydro-furo[3,4-c]pyridin-1-yl)-benzonitrile (110 mg) was dissolved in ethanol (5 mL) and then treated with sodium borohydride (51 mg). The reaction mixture was stirred for 1 hour, diluted with ethyl acetate and washed with brine. The organic layer was dried over sodium sulfate, concentrated, and the residue purified by flash chromatography to yield 3-[hydroxy-(3-hydroxymethyl-pyridin-4-yl)-methyl]-benzonitrile as a colorless foam.

$^1$HNMR (DMSO-$d_6$, 300 MHz) δ (ppm) 8.53 (s,1H), 8.49 (d, J=5.4 Hz, 1H), 7.8-7.4 (m, 5H), 6.29 (d, J=4.2 Hz, 1H), 6.04 (d, J=4.2 Hz, 1H), 5.37 (t, J=5.4 Hz,1H), 4.53 (m, 2H);
LCMS: 0.544 min, m/z: 241 (M+1).

EXAMPLE 55

[3-(Hydroxy-phenyl-methyl)-pyridin-4-yl]-phenyl-methanone (Compound #43)

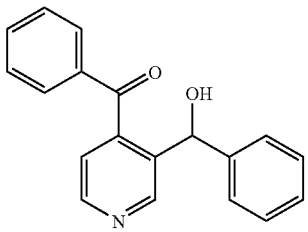

To a solution of 4-benzoyl-pyridine-3-carbaldehyde (97 mg, ol) in THF (5 mL) at −78° C. was added 1.0M phenylmagnesium bromide in THF (0.46 mL) and the reaction mixture stirred for 15 min. The reaction mixture was then quenched with aqueous ammonium chloride and extracted with ethyl acetate. The organic layer was dried over sodium sulfate, concentrated, and the residue purified by preparation TLC of silica gel with 10% methanol in dichloromethane to yield [3-(hydroxy-phenyl-methyl)-pyridin-4-yl]-phenyl-methanone as white crystals.

LCMS: 3.107 min, m/z: 290 (M+1).

EXAMPLE 56

[3-(1-Hydroxy-ethyl)-pyridin-4-yl]-phenyl-methanone (Compound #59)

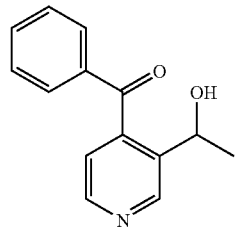

To a solution of 4-benzoyl-pyridine-3-carbaldehyde (114 mg, 0.54 mmol) in THF (3 mL) at −78° C. was added 3.0 M methylmagnesium bromide in THF (0.27 mL) and the reaction mixture was stirred for 15 min. The reaction mixture was then quenched with aqueous ammonium chloride and extracted with ethyl acetate. The organic layer was dried over sodium sulfate, concentrated, and the residue purified by chromatography of silica gel with 5% methanol in dichloromethane to yield [3-(1-hydroxy-ethyl)-pyridin-4-yl]-phenyl-methanone as white crystals.

LCMS: 2.118 min, m/z: 228 (M+1).

EXAMPLE 57

{3-[(4-Dimethylamino-phenyl)-hydroxy-methyl]-pyridin-4-yl}-phenyl-methanone (Compound #44)

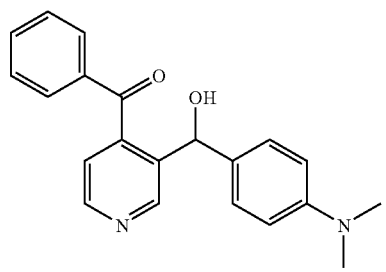

To a solution of 4-benzoyl-pyridine-3-carbaldehyde (62 mg, 0.29 mmol) in THF (3 mL) at −78° C. was added 0.5 M 4-(N,N-dimethyl)magnesium bromide in THF (0.88 mL) and the reaction mixture was stirred for 15 min. The reaction mixture was then quenched with aqueous ammonium chloride and extracted with ethyl acetate. The organic layer was dried over sodium sulfate, concentrated, and the residue purified by chromatography of silica gel with 5% methanol in dichloromethane to yield 3-[(4-dimethylamino-phenyl)-hydroxy-methyl]-pyridin-4-yl)-phenyl-methanone as a yellow solid.

LCMS: 2.195 min, m/z: 333 (M+1).

EXAMPLE 58

{3-[(3-Fluoro-4-methoxy-phenyl)-hydroxy-methyl]-pyridin-4-yl}-phenyl-methanone (Compound #45)

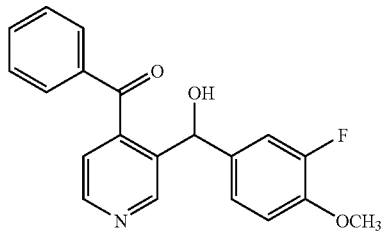

To a solution of 4-benzoyl-pyridine-3-carbaldehyde (62 mg, 0.29 mmol) in THF (3 mL) at −78° C. was added 0.5 M 4-(N,N-dimethyl)magnesium bromide in THF (0.88 mL) and the reaction mixture was stirred for 15 min. The reaction mixture was then quenched with aqueous ammonium chloride and extracted with ethyl acetate. The organic layer was dried over sodium sulfate, concentrated, and the residue purified by chromatography of silica gel with 5% methanol in dichloromethane to yield {3-[(3-fluoro-4-methoxy-phenyl)-hydroxy-methyl]-pyridin-4-yl}-phenyl-methanone as a white solid.

LCMS: 2.353 min, m/z: 338 (M+1).

EXAMPLE 59

{3-[(2,5-Dimethoxy-phenyl)-hydroxy-methyl]-pyridin-4-yl}-phenyl-methanone (Compound #46)

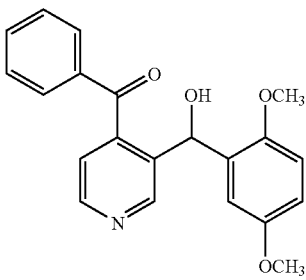

To a solution of 4-benzoyl-pyridine-3-carbaldehyde (110 mg, 0.52 mmol) in THF (3 mL) at −78° C. was added 1.0 M 2,5-dimethoxymagnesium bromide in THF (1.04 mL) and the reaction mixture was stirred for 15 min. The reaction mixture was then quenched with aqueous ammonium chloride and extracted with ethyl acetate. The organic layer was dried over sodium sulfate, concentrated, and the residue purified by chromatography of silica gel with 5% methanol in dichloromethane to yield {3-[(2,5-dimethoxy-phenyl)-hydroxy-methyl]-pyridin-4-yl}-phenyl-methanone as a white solid.

LCMS: 2.382 min, m/z: 350 (M+1).

EXAMPLE 60

{3-[(3-Fluoro-phenyl)-hydroxy-methyl]-pyridin-4-yl}-phenyl-methanone (Compound #47)

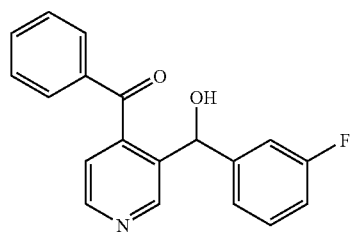

To a solution of 4-benzoyl-pyridine-3-carbaldehyde (80 mg, 0.38 mmol) in THF (3 mL) at −78° C. was added 1.0 M 3-fluoromagnesium bromide in THF (0.76 mL) and the reaction mixture was stirred for 15 min. The reaction mixture was then quenched with aqueous ammonium chloride and extracted with ethyl acetate. The organic layer was dried over sodium sulfate, concentrated, and the residue purified by chromatography of silica gel with 5% methanol in dichloromethane to yield {3-[(3-fluoro-phenyl)-hydroxy-methyl]-pyridin-4-yl}-phenyl-methanone as a white solid.

LCMS: 2.458 min, m/z: 308 (M+1).

EXAMPLE 61

3-[3-(Hydroxy-phenyl-methyl)-pyridine-4-carbonyl]-benzonitrile (Compound #48)

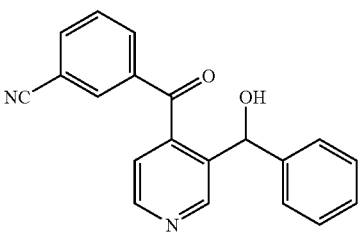

To a solution of 4-benzoyl-pyridine-3-carbaldehyde (111 mg, 0.47 mmol) in THF (5 mL) at −78° C. was added 1.0 M phenylmagnesium bromide in THF (0.47 mL) and the reaction mixture was stirred for 15 min. The reaction mixture was then quenched with aqueous ammonium chloride and extracted with ethyl acetate. The organic layer was dried over sodium sulfate, concentrated, and the residue purified by chromatography of silica gel with 5% methanol in dichloromethane to yield 3-[3-(hydroxy-phenyl-methyl)-pyridine-4-carbonyl]-benzonitrile as white crystals.

LCMS: 2.603 min, m/z: 315 (M+1).

EXAMPLE 62

3-(1,3-Dihydro-furo[3,4-c]pyridin-1-yl)-benzonitrile (Compound #66)

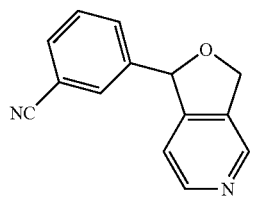

3-[Hydroxy-(3-hydroxymethyl-pyridin-4-yl)-methyl]-benzonitrile (100 mg, 0.42 mmol) and tosyl chloride (96 mg, 0.50 mmol) were dissolved in dichloromethane (5 mL) and then the reaction mixture was treated with triethylamine (0.09 mL, 0.65 mmol). The reaction mixture was stirred overnight at room temperature, then diluted with ethyl acetate and washed with 5% sodium bicarbonate. The organic layer was dried over sodium sulfate, concentrated, and the residue purified by chromatography of silica gel with 30% ethyl acetate in hexane to yield 3-(1,3-dihydro-furo[3,4-c]pyridin-1-yl)-benzonitrile as a white solid.

EXAMPLE 63

Potassium Channel Assay

TE671 human medulloblastoma cells were obtained from ATCC and grown in Dulbecco's modified Eagle's medium (DMEM) supplemented with 10% fetal bovine serum, 100 U/ml penicillin and 100 U/ml streptomycine.

The day before testing, the cells were plated in black 96-well plates at 50K/well. On the day of testing, the growth media was removed, then 100 µl of FLIPR buffer (20 mM HEPES, 120 mM NaCl, 2 mM KCl, 2 mM $CaCl_2$, 1 mM $MgCl_2$, 5 mM Glucose) and 100 µl of Membrane Potential Assay Dye (Molecular Devices) dissolved in FLIPR buffer were added to each well. The cells were incubated at room temperature for 15 to 30 min.

The effect of test compounds on KATP channels were evaluated on a fluorometric imaging plate reader (FLIPR, Molecular Devices) at room temperature. After a baseline period, 50 µl of 5× stock solution of test compound prepared in FLIPR buffer was added and fluorescence change was monitored for 3 minutes. After this reading, glyburide, a KATP channel blocker, was added to a final concentration of 5 µM to check the specificity of the test compound as a KATP channel opener. Hyperpolarization resulting from KATP channel opening was observed as a decrease in fluorescence intensity.

Representative compounds of the present invention were tested according to the procedure described above, with results as listed in Table 7 below.

TABLE 7

| ID No. | % Stimulation | $EC_{50}$ (µM) |
| --- | --- | --- |
| 1 | 36 | >30 |
| 2 | 23 | >30 |
| 3 | 19 | >30 |
| 4 | 38 | >30 |
| 5 | 33 | >30 |
| 6 | 42 | >30 |
| 7 | 2 | >30 |
| 8 | 31 | >30 |
| 9 |  | 7.73 |
| 10 | 22 | >30 |
| 11 | 2 | >30 |
| 12 | 20 | >30 |
| 13 | 0 | >30 |
| 14 |  | 4.56 |
| 15 |  | 6.27 |
| 19 |  | 9.63 |
| 20 |  | 19.43 |
| 21 |  | 23.20 |
| 22 |  | 15.14 |
| 23 |  | 11.41 |
| 24 |  | 14.45 |
| 25 |  | 9.82 |
| 26 |  | 10.19 |
| 27 |  | 10.71 |
| 28 |  | 10.19 |
| 29 |  | 13.74 |
| 30 | 7 | >30 |
| 31 |  | 15.03 |
| 32 |  | 8.48 |
| 33 | 40 | >30 |
| 34 |  | 20.84 |
| 35 | 37 | >30 |
| 36 | 24 | >30 |
| 37 |  | 9.59 |
| 38 | 63 | >30 |
| 39 |  | 10.47 |
| 43 |  | 17.36 |
| 44 |  | 17.41 |
| 45 |  | 11.61 |
| 46 |  | 12.15 |
| 47 |  | 5.09 |
| 48 |  | 14.34 |
| 50 | 19 | >30 |
| 51 | 48 | >30 |
| 52 |  | 17.24 |
| 53 | 30 | >30 |
| 55 | 24 | >30 |
| 56 | 33 | >30 |
| 57 | 16 | >30 |
| 58 | 14 | >30 |
| 59 |  | 26.81 |
| 63 |  | 7.97 |
| 65 | 34 | >30 |
| 66 |  | 8.19 |

EXAMPLE EXTRA1

As a specific embodiment of an oral composition, 100 mg of the compound prepared as in Example 62 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (II)

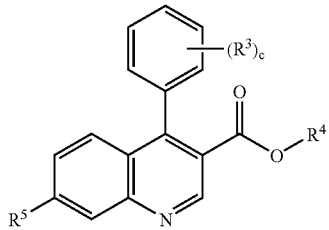

(II)

wherein
c is an integer from 0 to 2;
R$^3$ is selected from the group consisting of halogen, alkyl, halogenated alkyl, hydroxy substituted alkyl, alkoxy, cyano, alkyl-carbonyl-, alkoxy-carbonyl-, formyl and phenyl;
R$^4$ is selected from the group consisting of C$_{1-4}$alkyl;
R$^5$ is selected from the group consisting of methyl and trifluoromethyl;
or a pharmaceutically acceptable salt thereof.

2. A compound as in claim 1, wherein
c is an integer from 0 to 2;
R$^3$ is selected from the group consisting of halogen, cyano, C$_{1-4}$alkyl, C$_{1-4}$alkoxy, halogenated C$_{1-4}$alkyl, hydroxy substituted C$_{1-4}$alkyl, C$_{1-4}$alkyl-carbonyl-, C$_{1-4}$alkoxy-carbonyl-, formyl and phenyl;
R$^4$ is selected from the group consisting of C$_{1-4}$alkyl;
R$^5$ is trifluoromethyl;
or a pharmaceutically acceptable salt thereof.

3. A compound as in claim 2, wherein
c is an integer from 0 to 2;
R$^3$ is selected from the group consisting of fluoro, cyano, methyl, methoxy, trifluoromethyl, hydroxy-methyl-, methyl-carbonyl-, ethoxy-carbonyl-, formyl and phenyl;
R$^4$ is ethyl;
R$^5$ is trifluoromethyl;
or a pharmaceutically acceptable salt thereof.

4. A compound as in claim 3, selected from the group consisting of 4-(5-formyl-2-methoxy-phenyl)-7-trifluoromethyl-quinoline-3-carboxylic acid ethyl ester;
4-(5-hydroxymethyl-2-methoxy-phenyl )-7-trifluoromethyl-quinoline-3-carboxylic acid ethyl ester;
and pharmaceutically acceptable salts thereof.

5. A pharmaceutical composition comprising a pharmaceutically acceptable carrier and a compound of claim 1.

6. A pharmaceutical composition made by mixing a compound of claim 1 and a pharmaceutically acceptable carrier.

7. A process for making a pharmaceutical composition comprising mixing a compound of claim 1 and a pharmaceutically acceptable carrier.

* * * * *

UNITED STATES PATENT AND TRADEMARK OFFICE
CERTIFICATE OF CORRECTION

PATENT NO. : 7,790,895 B2
APPLICATION NO. : 11/360084
DATED : September 7, 2010
INVENTOR(S) : Jain et al.

It is certified that error appears in the above-identified patent and that said Letters Patent is hereby corrected as shown below:

Column 56
Line 9, delete "trifl  uoromethyl" and insert --trifluoromethyl--

Column 56
Line 18 & 19, delete "4-(5-hydroxymethyl-2-methoxy-phenyl   )-7-trifluoromethyl-quinoline-3-carboxylic acid ethyl ester;"
and insert --4-(5-hydroxymethyl-2-methoxy-phenyl)-7-trifluoromethyl-quinoline-3-carboxylic acid ethyl ester;--

Signed and Sealed this
Twelfth Day of April, 2011

David J. Kappos
*Director of the United States Patent and Trademark Office*